(12) United States Patent
Bae et al.

(10) Patent No.: US 12,274,896 B2
(45) Date of Patent: Apr. 15, 2025

(54) ULTRASONIC COMMUNICATION IN MEDICAL DEVICES

(71) Applicant: NuVasive Specialized Orthopedics, Inc., San Diego, CA (US)

(72) Inventors: Youngsam Bae, Los Angeles, CA (US); Khoa Pham, Garden Grove, CA (US); Niels Smidth, Laguna Beach, CA (US); Everett Van Zuiden, Chula Vista, CA (US); Jorge Lopez Camacho, Aliso Viejo, CA (US); Michael Moeller, Aliso Viejo, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 171 days.

(21) Appl. No.: 18/151,899

(22) Filed: Jan. 9, 2023

(65) Prior Publication Data
US 2023/0158338 A1    May 25, 2023

Related U.S. Application Data

(63) Continuation of application No. 16/785,240, filed on Feb. 7, 2020, now Pat. No. 11,577,097.
(Continued)

(51) Int. Cl.
*A61N 7/00* (2006.01)
*A61B 8/00* (2006.01)
(Continued)

(52) U.S. Cl.
CPC .............. *A61N 7/00* (2013.01); *A61B 8/4272* (2013.01); *A61B 8/565* (2013.01); *A61F 2/02* (2013.01);
(Continued)

(58) Field of Classification Search
CPC .......... A61B 2560/0481; A61B 8/0875; A61B 8/4227; A61B 8/4272; A61B 8/565; A61F 2/02; A61F 2/481; A61F 2002/30537; A61N 2007/0013; A61N 2007/0052; A61N 2007/0078; A61N 7/00; G16H 40/63;
(Continued)

(56) References Cited

U.S. PATENT DOCUMENTS

| 2,702,031 A | 2/1955 | Leslie |
| 3,111,945 A | 11/1963 | Von Solbrig |

(Continued)

FOREIGN PATENT DOCUMENTS

| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Mark D Remaly

(57) ABSTRACT

The present disclosure provides implants, sensor modules, networks, and methods configured to establish transcutaneous power and transcutaneous bidirectional data communication using ultrasound signals between two or more medical devices located on and within a body of a patient.

17 Claims, 19 Drawing Sheets

Related U.S. Application Data

(60) Provisional application No. 62/959,357, filed on Jan. 10, 2020, provisional application No. 62/802,457, filed on Feb. 7, 2019.

(51) Int. Cl.
  *A61F 2/02* (2006.01)
  *G16H 40/63* (2018.01)
  *A61B 8/08* (2006.01)
  *A61F 2/30* (2006.01)
  *A61F 2/48* (2006.01)

(52) U.S. Cl.
  CPC ............ *G16H 40/63* (2018.01); *A61B 8/0875* (2013.01); *A61B 8/4227* (2013.01); *A61B 2560/0481* (2013.01); *A61F 2002/30537* (2013.01); *A61F 2/481* (2021.08); *A61N 2007/0013* (2013.01); *A61N 2007/0052* (2013.01); *A61N 2007/0078* (2013.01)

(58) Field of Classification Search
  CPC .......... H04Q 2209/40; H04Q 2209/43; H04Q 2209/823; H04Q 2209/88; H04Q 9/00
  See application file for complete search history.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,170,488 B1 | 1/2001 | Spillman, Jr. et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |

(56) References Cited

U.S. PATENT DOCUMENTS

| | | |
|---|---|---|
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,082,041 B1 | 12/2011 | Radziemski |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,388,553 B2 | 3/2013 | James et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |

(56) References Cited

U.S. PATENT DOCUMENTS

| | | |
|---|---|---|
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,721,643 B2 | 5/2014 | Morgan et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,866 B2 | 12/2014 | Nycz |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,974,366 B1 | 3/2015 | Radziemski et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 10,252,066 B2 | 4/2019 | Radziemski et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0238992 A1 | 10/2007 | Donofrio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0046037 A1 | 2/2008 | Haubrich et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |

(56) References Cited

U.S. PATENT DOCUMENTS

| | | |
|---|---|---|
| 2008/0190237 A1 | 8/2008 | Radinger et al. |
| 2008/0228186 A1 | 9/2008 | Gall et al. |
| 2008/0228231 A1 | 9/2008 | Raphael et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0270949 A1 | 10/2009 | Kalpin et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0130240 A1 | 5/2012 | Sakamoto et al. |
| 2012/0157889 A1 | 6/2012 | Tanis et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0178915 A1 | 7/2013 | Radziemski et al. |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2013/0345566 A1 | 12/2013 | Weitzel et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0336474 A1 | 11/2014 | Arbabian et al. |
| 2014/0343350 A1 | 11/2014 | Martinson et al. |
| 2014/0358150 A1 | 12/2014 | Kaufman et al. |
| 2015/0080639 A1 | 3/2015 | Radziemski et al. |
| 2015/0105782 A1 | 4/2015 | D'Lima et al. |
| 2015/0105824 A1 | 4/2015 | Moskowitz et al. |
| 2015/0257799 A1 | 9/2015 | Janna et al. |
| 2015/0335285 A1 | 11/2015 | Poon et al. |
| 2016/0302721 A1* | 10/2016 | Wiedenhoefer ...... A61B 5/1071 |
| 2017/0125892 A1 | 5/2017 | Arbabian et al. |
| 2017/0135671 A1 | 5/2017 | Nowak et al. |
| 2017/0279571 A1 | 9/2017 | Melodia et al. |
| 2017/0319858 A1 | 11/2017 | Radziemski et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| JP | 2012507340 A | 3/2012 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | 2008018612 A1 | 2/2008 |
| WO | WO2011116158 A3 | 9/2011 |
| WO | WO2013119528 A1 | 8/2013 |
| WO | WO2014040013 A1 | 3/2014 |
| WO | 201817591 A9 | 1/2018 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

(56) References Cited

OTHER PUBLICATIONS

Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics, 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.

(56) References Cited

OTHER PUBLICATIONS

Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.

(56) References Cited

OTHER PUBLICATIONS

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

\* cited by examiner

ULTRASONIC COMMUNICATION IN MEDICAL DEVICES

PRIORITY CLAIM

This continuation application claims priority to co-pending application Ser. No. 16/785,240 filed on Feb. 7, 2020, entitled ULTRASONIC COMMUNICATION IN MEDICAL DEVICES, which claims priority to US provisional patent applications numbered 62/959,357 filed Jan. 10, 2020 and 62/802,457 filed Feb. 7, 2019, the contents of which is hereby incorporated by reference.

FIELD OF DISCLOSURE

The present disclosure generally relates to the field of ultrasound communication. More specifically, the present disclosure includes medical devices configured for bidirectional communication using ultrasound signals.

BACKGROUND

Medical implants have various forces exerted on them in vivo, especially medical implants that are adjustable in situ. Such adjustable medical implants for example, are used in limb lengthening and spinal adjustable surgical procedures to treat conditions such as limb deformities and scoliosis. Typically, these adjustable medical implants are secured to one or more bones and gradually adjusted over time until some patient outcome is achieved.

These surgical implants and procedures do not include an accurate and non-invasive means of measurement of in vivo conditions, such as forces and pressures, present at the implant site. Particularly, during the course of treatment. A need exists for a device and method to facilitate the ability of care providers to non-invasively ascertain conditions present at the implant.

SUMMARY OF THE INVENTION

The present disclosure provides transcutaneous ultrasonic power transmission and bidirectional data communication between medical devices located on and/or within a body of a patient.

In some aspects, the present disclosure provides a system including: an implant and an external transceiver, the implant having at least one ultrasonic transducer configured to receive an ultrasound signal sent by the external transceiver and convert that ultrasound signal to electrical energy to power the implant.

In some aspects, the present disclosure provides an implant including a sensor and an ultrasonic transducer, wherein the sensor is configured to measure a physical property of the implant, and wherein the implant is configured to transmit data corresponding the measurement via an ultrasound signal produced by the ultrasonic transducer.

In some aspects, the present disclosure provides an adjustable implant, the adjustable implant including an actuator and at least one ultrasonic transducer, wherein the ultrasonic transducer is configured to receive an ultrasound signal sent by an external transceiver, and convert that ultrasound signal to electrical energy to power the actuator, and wherein the implant is configured for the bidirectional ultrasonic data communication using the ultrasonic transducer to send and receive adjustment instructions between the adjustable implant and the external transceiver.

In some aspects, the present disclosure provides a sensor module configured to be integrated with an implant, the sensor module including: a sensor, an ultrasonic transducer, and a controller, wherein the sensor, ultrasonic transducer, and controller are operably connected, and wherein the sensor module is configured for bidirectional data communication using ultrasound signals.

In some aspects, the present disclosure provides an external transceiver configured to be placed adjacent to a patient's skin having at least one ultrasonic transducer, wherein the at least one ultrasonic transducer is configured for bidirectional data communication using ultrasound signals.

In some aspects, the present disclosure provides a method of transcutaneous transmission of power to an implant positioned within a subject via an ultrasound signal.

In some aspects, the present disclosure provides a method of transcutaneous transmission of power to an implant using an ultrasound signal including: transmitting an ultrasound signal from an external transceiver to the implant, receiving the ultrasound signal at the implant with an ultrasonic transducer; converting the signal to electrical energy using the ultrasonic transducer; and using the electrical energy to power the implant.

In some aspects, the present disclosure provides a method of transcutaneous bidirectional data communication using an ultrasound signal, the method including: placing an implant within a body of a patient, placing a transceiver on or within the body of the patient, and transcutaneously transmitting ultrasound signals between the implant and the transceiver.

In some aspects, the present disclosure provides a method of transcutaneous bidirectional data communication using an ultrasound signal, the method including: implanting a device within a body of a patient, transmitting at least one of power or data to the device using an ultrasound signal, and transmitting data from the device using an ultrasound signal.

In some aspects, the present disclosure provides a method of c using an ultrasound signal, the method comprising the steps of: implanting a sensor module within a body of a patient, transmitting at least one of wireless power or data to the sensor module using an ultrasound signal; and transmitting data from the sensor module using an ultrasound signal.

In some aspects, the present disclosure provides a local body area network (BAN), the local body area network includes one or more implants configured for transcutaneous bidirectional data communication, allowing the one or more implants to communicate data across the local body area network transcutaneously.

In some aspects, the present disclosure provides a local body area network (BAN), the local body area network includes an external transceiver configured for transcutaneous ultrasonic communication, and one or more implants configured for transcutaneous ultrasonic communication, wherein the external transceiver and the one or more implants are configured to communicate data across the local body area network (BAN).

BRIEF DESCRIPTION OF THE DRAWINGS

These and other features will be further understood by those with skill in the art upon a review of the appended drawings, wherein.

DETAILED DESCRIPTION OF THE PREFERRED EMBODIMENTS

Figure 1:
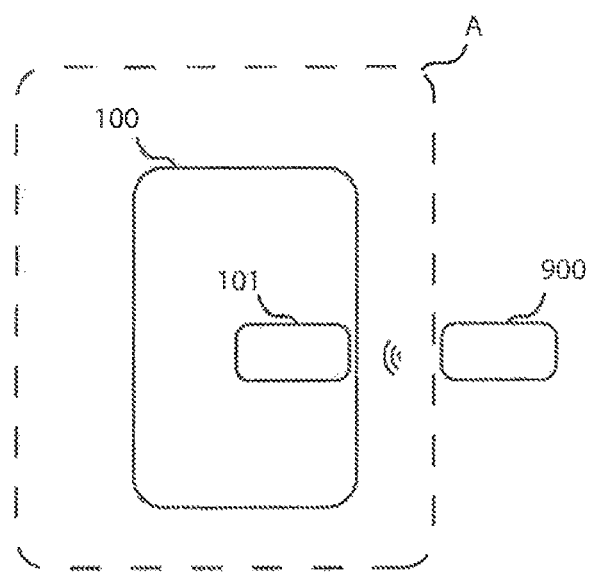
FIG. 1 shows an implant in accordance with a first embodiment disposed within a patient, the implant configured to receive power transcutaneously via an ultrasound signal.

For purposes of explanation and not limitation, details and descriptions of certain embodiments are hereinafter provided such that one having ordinary skill in the art may be enabled to make and use the invention. These details and descriptions are representative only of certain embodiments, however, and a myriad of other embodiments which will not be expressly described will be readily understood by those having skill in the art upon a thorough review hereof. Accordingly, any reviewer of the instant disclosure should interpret the scope of the invention by the claims, and such scope shall not be limited by the embodiments described and illustrated herein.

Ultrasonic communication in medical implants can provide one or more of: power, enhanced control, and feedback between medical implants and/or external transceivers.

In Radio Frequency (RF) signals, which utilize electromagnetic waves, information may be conveyed within the body. But RF signals experience large amounts of attenuation in aqueous tissues, bone tissues, and largely reflect off metallic surfaces. Ultrasound waves experience much less attenuation within aqueous tissues, bone tissues, and can even penetrate through metallic surfaces. Ultrasound signals are ultrasound waves that convey information via known amplitude and phase shifting techniques, similar to common techniques used in RF telecommunication. Phase-Shift Keying is a digital modulation process which conveys data by changing the phase of a constant frequency carrier wave. The modulation is accomplished by varying the sine and cosine inputs at a precise time. It is widely used for wireless LANs, RFID and Bluetooth (BT). Binary phase-shift keying (BPSK) or any known modulation technique may be used in ultrasound communication including: On-Off Keying (OOK), Amplitude-Shift Keying (ASK) and Frequency-Shift Keying (FSK).

The frequency of ultrasound sound waves chosen to establish the bidirectional ultrasonic communication may include any frequency of ultrasound, but are generally greater than about 20 kilohertz. In some embodiments, the frequency of ultrasound sound waves may be between 200 and 400 kilohertz, for example about 300 kilohertz. The benefits of utilizing ultrasound sound waves for power and data transmission include: (1) that ultrasound sound waves have favorable propagation and minimal attenuation characteristics through metal or solid mediums (e.g., metallic medical implants), and (2) that ultrasound sound waves transmit data transcutaneously through various aqueous tissues in animals (e.g. human skin, muscle and bone).

Once a transcutaneous bidirectional ultrasound communication link is established, the implant may have a power consumption of between 0.5 mW and 80 mW, 1 mW and 60 mW, and 2.0 mW and 40 mW, 10 mW, 5 mW, and any subrange thereof. The ultrasonic transducer may consume about 20 mW of power when in operation. The ultrasonic transducer may be configured to transmit data through at least four inches of water or aqueous tissues at a rate of 5 values per second (1 kb/s) with a data reliability of over 95%. Data reliability transmitted from the ultrasonic transducer at these power levels may be at least 95%, at least 98%, at least 99%, at least 99.9%, or 100%. "Data reliability" means reliability over 10 minutes as calculated from a bit error rate (BER).

As discussed above, ultrasonic communication in medical implants can provide one or more of: power, enhanced control, and biofeedback between medical implants and external transceivers. Ultrasonic communication in medical implants includes of one or more of power transmission and data transmission using ultrasound signals. The ultrasound signal may be one or more of filtered, demodulated, amplified, and analyzed using one or more of physical components and software techniques.

Communication may be established in one direction. In some embodiments, the external transceiver may transmit an ultrasound signal to the implant to transfer power from the external transceiver to the implant. As discussed above, the ultrasound signal may be modulated. The implant is configured to harvest electrical energy from the ultrasound signal and may include one or more of a filter, a mixer, and a modulator to configure the implant for power reception. In some embodiments, the circuitry of the implant may include one or more of a filter, a mixer, and a modulator with any known electrical components and circuitry to configure the implant for data communication. In some embodiments, one or more of a discrete demodulator and mixer may be implemented on the implant's controller.

For bidirectional communication, and communication across a network, the implant may communicate back to the external transceiver during one or more of a pause and a release the line time period, during which the external transceiver may cease signal transmission allowing the implant to send modulated ultrasound signals back to the transceiver. For example, the transceiver may act as a master and command or query the implant acting as a slave, then pause ultrasound signal transmission for a period and allow the slave implant to send an ultrasound signal and for example: confirm or reply to the query.

In some embodiments, bidirectional communication may include continuous power transmission. For example, the external transceiver sending a constant power signal to the implant. This power signal from external transceiver to implant may be modulated using the techniques above to transmit data from external transceiver to implant. The implant may communicate data back to the external transceiver via backscatter/load modulation. For example, the incident energy from the external transceiver may be reflected back by the implant towards the external transceiver to communicate.

In some embodiments the ultrasound transducer may be shorted by a switching device, for example a BJT or MOSFET on an integrated circuit. In some embodiments, the ultrasound transducer may be shorted by a switch, relay, solid state relay, vacuum tube, and any other known device configured to short the ultrasound transducer for backscattering/load modulation.

In some embodiments, power transmission may be sequential. For example, the external transceiver sending a pulsed power signal to the implant. This power signal from external transceiver to implant may be modulated using the techniques above to transmit data from external transceiver to implant. The implant may communicate data back to the external transceiver when during pauses in data transmission.

In the near field region (with the implant and the external transceiver in close proximity), adjusting the impedance of the load is known as load modulation. Due to the coupling of the relatively closely spaced transducers, a change in the impedance of the ultrasound transducer of the implant, will be observable by the external transceiver. The external transceiver's ultrasound transducer will appear to its driving circuit to change in impedance, and draw different amounts of current.

In the far field region (implant and external transceiver at a greater distance), adjusting the impedance of the load is known as backscatter communications. Changing the impedance of the implant's ultrasound transducer changes the magnitude of the reflected energy. Shorting out the implant's ultrasound transducer will result in increased reflection of energy. This reflected energy pattern may be visible at the external transceiver.

These and other data communication protocols may be readily understood by those having skill in the art. As one with skill in the art may appreciate, the above communication protocols are described with an implant communicating with an external transceiver. In some embodiments, each of the implant and the external transceiver can be replaced by one or more of: a second implant, a sensor module, and a tertiary device.

In FIG. 1, a schematic diagram is provided showing an implant 100 adapted to receive wireless power from an external transceiver 900 via an ultrasound signal. The ultrasound signal may include modulated ultrasound waves produced by an ultrasonic transducer. The implant 100 is shown disposed within a body of a patient A. The patient A may include any animal, and may be a human. The implant 100 may include at least one ultrasonic transducer 101 configured to receive an ultrasound signal sent by an external transceiver 900, and convert that ultrasound signal to electrical energy. The implant 100 may include for example a patch configured to be attached to one or more of a bone and a tissue within the patient. The ultrasonic transducer 101 may include for example a piezoelectric polyvinylidene fluoride (PVDF) flexible thin film piezoelectric transducer, which may be operably connected to other circuitry of the implant 100. The electrical energy harvested by the ultrasonic transducer 101 may be used to activate or power any circuitry of the implant 100.

In some aspects, the implant 100 may be, by way of example, a distraction rod, an intramedullary rod, or any other adjustable implant or medical device intended for placement on and within the body of a patient. Wireless activation and or powering of the implant 100 using ultrasound waves, may eliminate a need for the internal power storage devices required by some known adjustable implants.

The implant 100, may be made of Polyether ether ketone (PEEK), Polyetherketone (PEK), Titanium (Ti), and any other material known and used in the art of manufacture of medical implants. The material may be chosen depending on the application of the implant 100. The implant 100, may be fabricated using known fabrication, including known electronic fabrication techniques.

In some embodiments, the ultrasonic transducer 101 may include any device that induces sound waves or mechanical vibration, and converts soundwaves to electronic signals, including for example: a piezoelectric transducer, a single crystal ultrasonic transducer, a lead zirconate titanate (PZT) ultrasonic transducer, piezoelectric polyvinylidene fluoride (PVDF) ultrasonic transducer, capacitive micromachined ultrasonic transducers (CMUT), piezoelectric micromachined ultrasonic transducers (CMUT), or any ultrasonic transducer known and used in the art. In some embodiments, the ultrasonic transducer 101 may include one or more of: a thin film ultrasonic transducer, a flat ultrasonic transducer, a tubular ultrasonic transducer. A benefit for example of a thin film ultrasonic transducer is the reduced thickness of the ultrasonic transducer. A benefit for example of a flat ultrasonic transducer is improved transmission and reception characteristics. A benefit for example of a tubular ultrasonic transducer is multi-directional transmission and reception. The type of ultrasonic transducer may be chosen to complement the application of the implant 100.

In some embodiments, the external device 900 may retrieve an ID tag of an implant 100 using ultrasound waves. For example, the implant 100 may include an integrated circuit and an ultrasonic transceiver 101, which are used to transmit data corresponding to an ID tag of the implant 100 to the external device 900 using ultrasound waves. The external device 900 may transmit an ultrasound signal modulated at a particular temperance to the implant 100. Upon receipt, the modulated ultrasound signal will be converted to electrical power by the ultrasonic transducer and may activate a digital switch of the implant 100. Upon activation, the implant may transmit a modulated ultrasound signal corresponding to the ID tag, back to the external device 900. Allowing a user to determine the ID tag and corresponding implant 100 without for example taking unnecessary radiological images which may expose the patient to radiation.

In some embodiments, a phased array containing multiple ultrasonic transducers may be provided to one or more of the external device and the implant to provide enhanced reception capabilities to the implant or external device.

Figure 2:
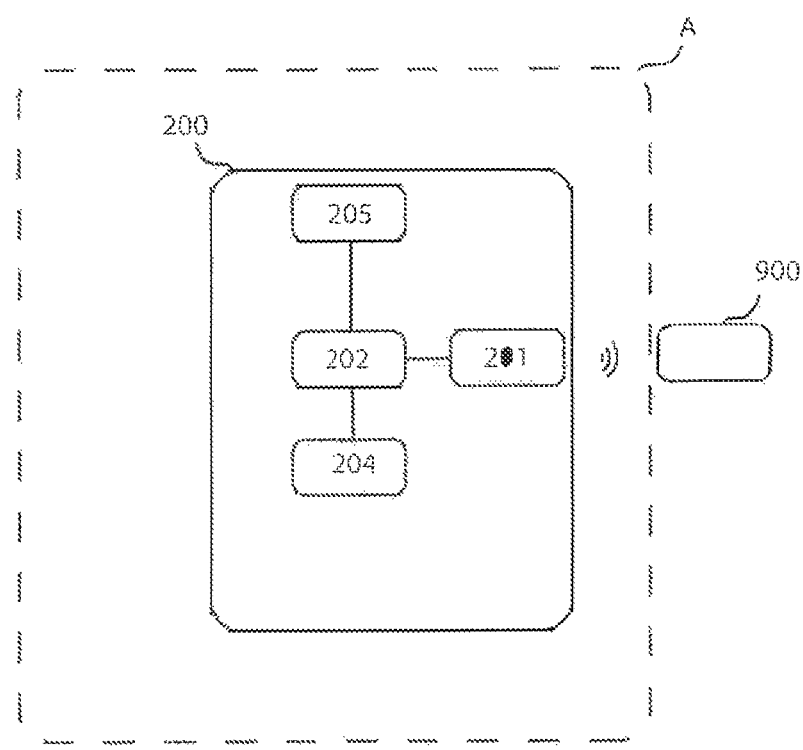
FIG. 2 shows an implant in accordance with a second embodiment, the implant configured for transcutaneous bidirectional ultrasonic data communication with an external transceiver.

Turning to FIG. 2, a schematic diagram is provided showing implant 200 in accordance with a second embodiment, the implant 200 is configured for transcutaneous ultrasonic data communication with at least an external transceiver 900. The implant 200 is shown having operatively connected circuitry including at least one ultrasonic transducer 201, a controller 202, a sensor 205, and a power storage device 204. In some embodiments, one or more of these components may be duplicated, substituted, or withheld.

The controller 202 may be any type of controller 202 known and used in the art including: high performance microcontrollers (MCUs), Programmable System on Chip (PSoC), Application Specific Integrated Circuit (ASIC) or any other type of controller or microcomputer. The controller 202 may be disposed on a printed circuit board which may also contain other electronic circuitry and connect other electrical components including: Analog to Digital Converter (ADC), Digital to Analog Converter (DAC), op-amps, memory or any other electrical component. The controller may further include a frequency synthesizer (i.e., creates carrier waves for ultrasonic transducer 201), power amplifiers, noise filters (i.e., conditions carrier wave), power and read strain gauges (i.e., force sensor controls), and may be configured to adjust carrier waves, power, etc. such as by computer executable instructions that interface with a user via a graphical user interface, as discussed below.

A power storage device 204 may be provided. The power storage device 204 may include a battery, a capacitor, and any other power storage device. The power storage device 204 may include a rechargeable battery, for example a Lithium ion rechargeable battery. The power storage device may include a solid state battery and any battery including any known battery chemistry.

The implant 200 may include a charging circuit operably connected to one or more of the power storage device 204 and the piezoelectric transducer 201. The charging circuit may be at least partially integrated into for example the controller 202. The power storage device 204 may be operably connected to the controller 202 via any electronic conductor including wires, boards, and interconnects. The charging circuit may include any charging circuit known and used in the art.

The implant 200 may be configured to receive an ultrasound signal sent by an external transceiver 900, and convert that ultrasound signal to electrical energy using the ultrasonic transducer 201. The recharging circuit may use the generated electrical energy to charge the power storage device 204.

The external transceiver 900 may recharge a battery of the implant 200, by transmitting an ultrasound signal to the implant 100, with the piezo electric transducer configured to convert the ultrasound signal to electrical power to recharge the battery. In some embodiments, the external transceiver 900 may activate the implant 100 by sending pulses of ultrasound signal for "stop and go" charging of the capacitor. For example, the capacitor may be charged by a pulse or a series of pulses, with just enough energy to one or more of: make an incremental adjustment and send a signal back to the external transceiver. In some embodiments, real time charging of the power storage device can enable continuous drive of an actuator of the implant.

In some embodiments, other known wireless charging circuits and techniques including for example, inductive coupling and magnetic coupling may be used to wirelessly transfer power to the implant 200.

In some embodiments, an external transceiver 900 may activate the circuitry of the implant 200 by transmitting an ultrasound signal to the ultrasonic transducer 201. The ultrasound waves of the ultrasound signal may be received by the ultrasonic transducer 201 and converted into electrical energy. The controller 202 may be programmed such that upon receipt of ultrasound waves corresponding to a modulated signal, for example a particular step function of a particular temperance, the controller 202 will close an electrical switch and activate the implant 200. Similarly, in other embodiments a particular step function may be used to open an electrical switch and deactivate the implant 200 to conserve power stored in the power storage device 204.

In some embodiments, the controller 202 may be programmed to time the implant 200 out after a certain period of time, for example if the ultrasound transducer 201 has not sent or received an ultrasound signal for a test period of time, the controller 202 may deactivate the implant 200.

In some embodiments, the controller 202 may be programmed to turn off the power storage device 204 and to put the implant 200 to sleep for a certain period of time to conserve power. For example, the controller may activate the implant 200 for ¼ of 1 second to one or more of: transmit ultrasound signals using the ultrasound transducer 201, obtain measurements using the sensor 205, control an actuator, communicate with other electronics of the implant 200, etc. During this ¼ of the second the implant 200 is said to be "awake". The controller 202 may deactivate the implant 200 for ¾ of the second. During this ¾ of the second the device is said to be asleep.

In some embodiments the implant 200 may include one or more sensor 205 operably connected to the controller 202. The one or more sensor 205 may be designed to measure temperature, position, force, pressure, capacitance, resistance, and any other physical property or characteristic of the implant 200 or surrounding anatomical structures of the patient A. In some embodiments, the sensor may include for example a position sensor (e.g. optical sensor). In the illustrated embodiment, the sensor 205 may be configured to sense force or temperature for example.

In some embodiments, the sensor 205 may include a Micro-Electro-Mechanical-System (MEMS) sensor. These sensors provide a reduced profile (e.g. 1 pm-100 pm size). The MEMS sensor may include an accelerometer, pressure sensor, gas sensors, humidity sensor, a gyrosensor, ambient light sensor, optical sensor, gesture sensor, proximity sensor, position sensor, touch sensor, and may include any other known sensory functionality.

The sensor 205 may communicate a sensor reading to the controller 202, which may convert the reading to a modulated electrical signal. The modulated electrical signal may then be used to drive the ultrasonic transducer 201, which then transmits ultrasound waves at a frequency corresponding to the modulated electrical signal.

The controller 202 may change analogue information from the sensor to digital values and may drive modulation of the ultrasonic transducer 201, to transmit data using ultrasound waves. Any known signal modification technique for data transmission may be used for ultrasound waves that may be used for example with RF data transmission. Including any type of pass band modulation.

The implant 200 may include an adjustable implant. The adjustable implant may include any actuator known and used in the art. As one with skill in the art may appreciate, the actuator may include for example an electric motor, a rotatable magnet, an impact driver, and any known actuator used in medical implants. The implant 200 may be configured to harvest ultrasound waves transmitted by another implant or an external transceiver, and convert the ultrasound waves to electrical energy to power the actuator.

Figure 3A:
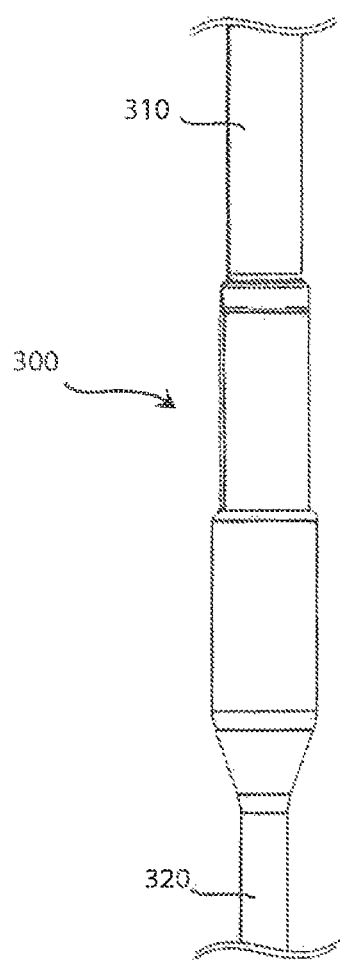
FIG. 3A shows a side view of an implant in accordance with a third embodiment, the implant configured for transcutaneous bidirectional data communication using an ultrasound signal, the implant including a sensor module disposed therein.
Figure 3B:
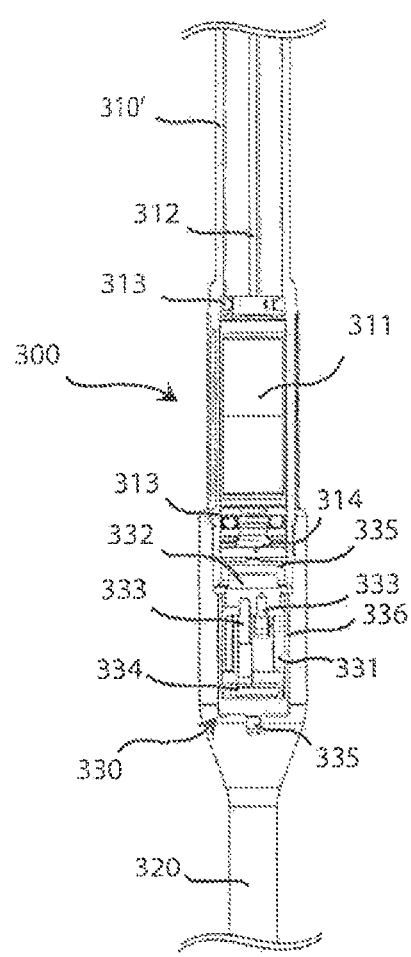
FIG. 3B shows a cross-sectional side view of the implant in accordance with the third embodiment, the implant shown having a sensor module disposed therein, the sensor module configured for transcutaneous bidirectional data communication using an ultrasound signal.

In FIG. 3A-3B, an adjustable implant 300 is shown. The adjustable implant 300 includes a first portion 310 configured to be attached to a bone of a patient at a first location and a second portion 320 configured to be attached to a bone of a patient at a second location. The adjustable implant 300 may be any type of adjustable implant. By way of example, an adjustable implant may include magnetically adjustable systems, such as the PRECICE® or MAGEC® magnetically adjustable implant systems for spinal and limb lengthening procedures sold by NuVasive, Inc. of San Diego, California. Such adjustable systems are disclosed in, for example, U.S. Pat. Nos. 9,398,925 and 9,393,117, which are incorporated by reference herein in their entireties.

FIG. 3B shows a cross-sectional view of the adjustable implant 300, the first portion 310 includes a distraction rod. The distraction rod comprises a magnet 311, and the magnet 311 is connected to a lead screw 312. Upon an axial rotation of the magnet 311 due to an externally applied rotating magnetic field, the lead screw 312 will rotate. Rotation of the lead screw 312 will cause an axial distraction of the distraction rod.

Now, adjustable implants experience numerous forces in vivo. For example, as the length of the illustrated distraction rod is increased, the distraction rod will experience axial forces pushing down through the lead screw on the magnet 311. Thrust bearings 313 are provided to mitigate the effect of these forces on the rotation of the magnet 311. However, when using an External Controller to noninvasively apply the magnetic field and adjust the distraction rod, biofeedback is often limited.

The implant 300 in FIG. 3B includes a sensor module 330 disposed within the second portion 320. The sensor module 330 includes a tubular piezoelectric transducer 331 operably connected to a controller 332. The tubular piezoelectric transducer 331 is configured to transmit and receive ultrasound signals. The tubular piezoelectric transducer 331 is operably connected to the controller 332 via an interconnect 333. As discussed above, the controller 332 may be any type of controller 332 known and used in the art including high performance microcontrollers (MCUs), Programmable System on Chip (PSoC), or any other type of controller. The controller 332 may be disposed on a printed circuit board which may also contain other electronic circuitry and components therein including: Analog to Digital Converter (ADC), Digital to Analog Converter (DAC), op-amps, memory and any other known electronic component.

A power storage device 334 is provided. The power storage device 334 may include a battery, a capacitor, and any other rechargeable power storage device.

The sensor module 330 may include a recharging circuit operably connected to the power storage device 334 and the tubular piezoelectric transducer 331. The recharging circuit may be for example: integrated into the controller 332 or disposed on another printed circuit board. The power storage device 334 may be operably connected to the controller 332 via an interconnect 333.

The sensor module 330 is configured to receive an ultrasound signal sent by an external transceiver 900, and convert that ultrasound signal to electrical energy using the tubular piezoelectric transducer 331. The recharging circuit may use the harvested electrical energy to charge the power storage device 334.

In some embodiments, an external transceiver 900 may activate the circuitry of the sensor module 330 by transmitting ultrasound waves to the sensor module 330. The ultrasound waves are received by the tubular piezoelectric transducer 331 and converted into electrical energy. The controller 332 may be programmed such that upon receipt of ultrasound waves corresponding to a particular modulated signal, for example a particular step function of particular temperance, the controller may close an electrical switch and activate the device. Similarly, in other embodiments a particular step function may open the electrical switch and deactivate the device to conserve power.

In some embodiments, the controller 332 may be programmed to time out after a certain period of time, wherein if for example the piezoelectric transducer 331 has not sent or received ultrasound waves, thereby conserving charged power levels of the power storage device 334, extending a battery life thereof.

In some embodiments the sensor module 330 may be configured to have a power consumption of between 0.5 mW and 80 mW, 1 mW and 60 mW, and 2.0 mW and 40 mW, 10 mW, 5 mW, or any subrange thereof. The transmitter 30 may consume about 20 mW of power when in operation. The transmitter 30 may be configured to transmit data at least four inches through water at a rate of 5 values per second (1 kb/s) with a data reliability of 95%. Data reliability transmitted from the transmitter at these power levels may be at least 95%, at least 98%, at least 99%, at least 99.9%, or 100%. "Data reliability" means reliability over 10 minutes as calculated from a bit error rate (BER).

The sensor module 330 may include one or more sensors 335 operably connected to the controller 332. The sensors 335 may be designed to measure force, temperature, pressure, capacitance, resistance, and any other type of sensor known and used in the art. In the instant embodiment the sensor module 330 is configured to sense axial force from the distraction device using a force sensor 335. The force sensor 335 of the sensor module 330 is operably coupled to the distraction rod using an adapter plate 314.

The force sensor 335 communicates a sensor reading to the controller 332, which may convert the reading to a modulated electrical signal. The modulated electrical signal may then be used to drive the piezoelectric transducer 331, which then transmits ultrasound waves transcutaneously to an external transceiver 900. In some embodiments, forms of modulation may include: on-off keying, amplitude shift keying (ASK), frequency shift keying (FSK), phase shift keying (PSK), analogue frequency modulation, or any other form of modulation commonly known and used for data transmission. Advantageously, signals that are modulated use less power than non-modulated signals and may be transmitted and received at greater distance from the sensor module 330 than non-modulated signals. Modulated signals may also have a greater accuracy than non-modulated signals.

In some embodiments, the sensor module 330 includes an encapsulation 336 providing a hermetic seal to the sensor module 330. In order to prevent air gaps which include pockets of unnecessary ultrasonic impedance, in some embodiments the piezoelectric transducer 331 is coupled to at least a portion of the encapsulation 336 using a conductive epoxy (see FIG. 4D, 408). In this embodiment the sensor module 330 is disposed adjacent to a surface of the implant 300 to minimize airgaps and impedance.

The conductive epoxy may include any ultrasound conductive material to reduce air gaps, including aluminum epoxy, copper epoxy, copper tape, Ti-epoxy, industry acoustic couplant, and any other material providing favorable electrical and acoustic conductive properties. When selecting a conductive epoxy one may consider: i.) impedance matching to improve the ultrasonic transmission efficiency between the implant and the piezoelectric transducer, and ii.) the circuit grounding the electronics.

The sensor module 330 may include a memory and may log data corresponding to one or more of a reading of the sensor 335, data received from the external transceiver 900 via ultrasound signals, and other data corresponding to the implant 300 and a biological condition of the patient. For example, the sensor module 330 may record sensor 335 data at various time intervals. In some embodiments data logging includes overwriting the data where needed to maintain files similar to for example a car dash camera.

Upon establishing a bidirectional communication link with an external transceiver 900 using ultrasound signals, the external transceiver 900 may download the data from the sensor module 330. A user may later retrieve the data from the external transceiver 900 and be able to plot the data, giving the user invaluable insights into the in-situ forces being placed on the implant 100.

In some embodiments, the external transceiver 900 may include a wired or RF communication capability and may additionally be accessible to a remote user through one or more of the internet, WiFi, Bluetooth, and cellular networks.

In some embodiments, the user can remotely update a firmware of the controller 332, for example across the internet by remotely accessing the external transceiver 900. In some embodiments, the user can transmit adjustment instructions to the implant 100, for example across the internet by remotely accessing the external transceiver 900. In some embodiments, the user can access data from the implant 100, for example across the internet by remotely accessing the external transceiver 900.

As one with skill in the art may appreciate, in the instant embodiment the implant 300 includes a sensor module 330 having various capabilities and features. In some other embodiments, these various components and features may be incorporated directly into the implant 300 similar to those discussed supra.

Figure 4A:
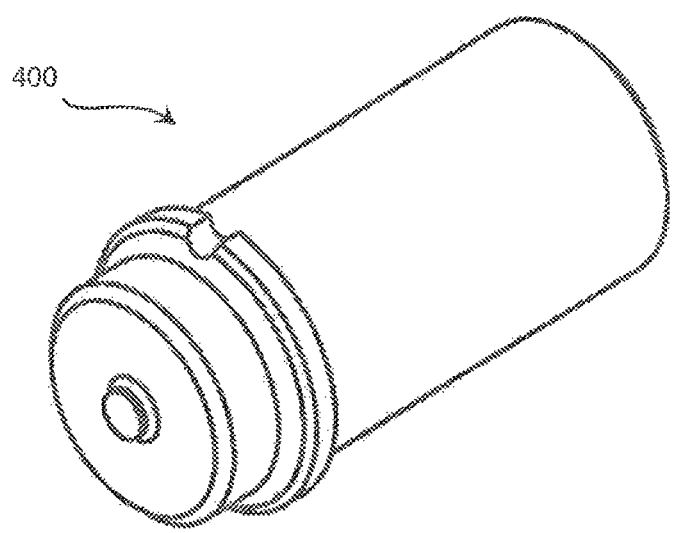
FIG. 4A shows a perspective view of a sensor module in accordance with a first embodiment.
Figure 4B:
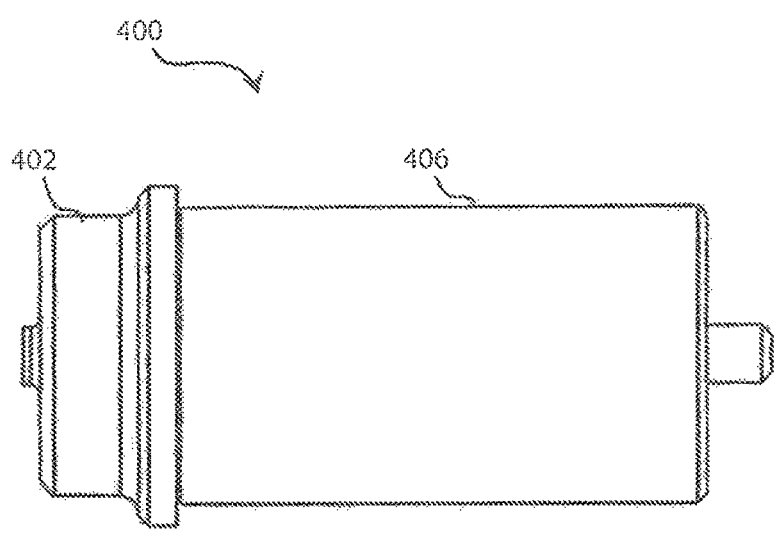
FIG. 4B shows a side view of the sensor module in accordance with the first embodiment.

FIG. 4A shows a perspective view of a sensor module 400. The sensor module 400 is configured to interface with any implant to provide at least one of remote activation, transcutaneous power, transcutaneous bidirectional ultrasonic data communication, or remote measurements of properties of the implant. FIG. 4B shows a side view of the sensor module 400, the sensor module 400 shown including an encapsulation 406 hermetically sealing the internal components of the sensor module 400 therein.

In the illustrated embodiment, the sensor module 400 has a cylindrical profile. As one with skill in the art may appreciate the sensor module 400 may conform to any profile including: a rectangular profile, a block profile, a disc profile, a patch, a membrane, and any known profile of an implant and a surface of an implant. Wherein the implant is a distraction rod, the cylindrical profile may provide some advantageous. For example, the cylindrical profile of the sensor module 400 is intended to allow a maximum amount of contact surface of the sensor module 400 across an internal surface of the distraction rod. Matching the curvature of the sensor module to the intended implant provides improved transmission and reception characteristics of the sensor module 400, across greater surface area of the implant, and provides up to 360 degrees of reception.

Figure 4C:
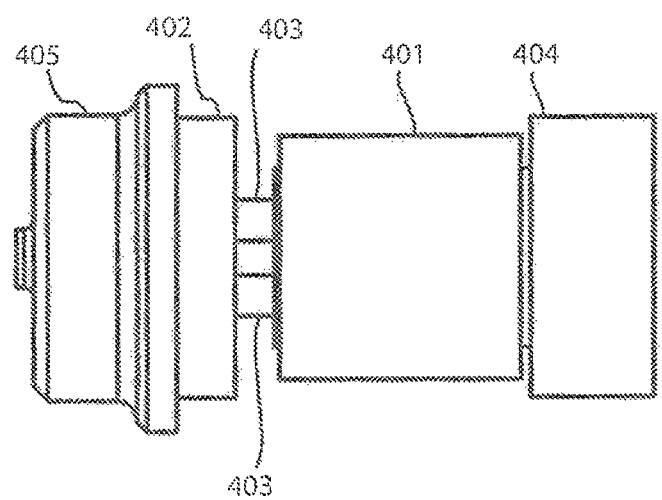
FIG. 4C shows a side view of the sensor module in accordance with the first embodiment, the sensor module shown with a portion of an external encapsulation removed.

In FIG. 4C, the sensor module 400 is shown with part of the encapsulation 406 removed for convenience, revealing some of the internal components of the sensor module 400. The sensor module 400 is shown having a tubular ultrasound transducer 401, a controller 402, at least one interconnect 403, a power storage device 404, and a sensor 405.

Figure 4D:
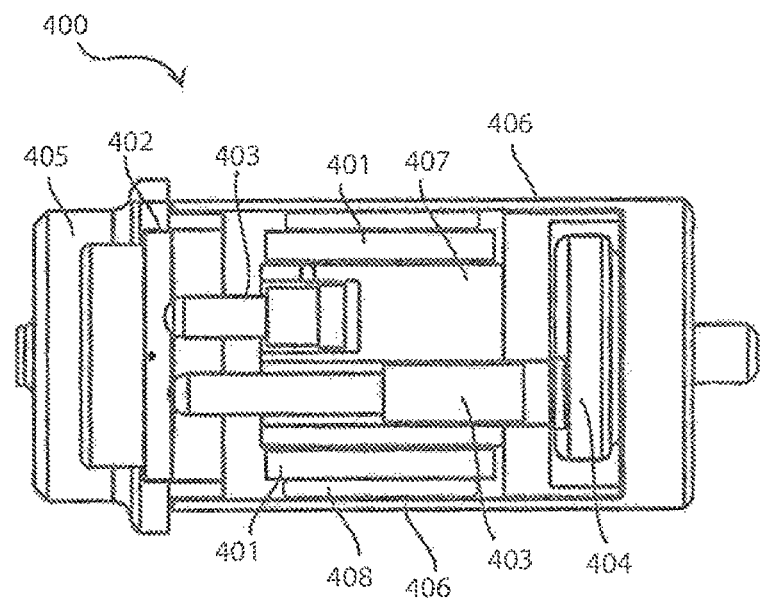
FIG. 4D shows a cross-sectional side view of the sensor module in accordance with the first embodiment, the sensor module shown including a three-dimensional stacked circuitry design.

In FIG. 4D a cross-sectional side view of the sensor module 400 is provided, revealing the internal circuitry and structure of the sensor module 400. In this embodiment the circuitry is arranged in a three dimensional stacked configuration. In this configuration the tubular ultrasonic transducer 401, power storage device 404, and controller 402 are stacked on top of one another and connected via interconnects 403. This stacked arrangement provides reduced dimensions to the sensor module 400. This stacked arrangement is achieved using the tubular piezoelectric transducer 401 and a specially designed chassis 407.

In some embodiments the ultrasonic transducer 401 is tubular, for example having a channel extending axially therethrough. In such embodiments, the ultrasonic transducer 401 may be coupled to a chassis 407 having interconnects extending therethrough. One interconnect 433 may be configured to operably connect the ultrasonic transducer 401 to a first terminal of the controller 402. The other interconnect 403 may be configured to operably connect the power storage device 404 to a second terminal of the controller 402. The controller 402 may interface with, be integrated with, or otherwise operably connected to a sensor 405.

In some embodiments, the ground terminal of the power storage device 404 may be shorted to the encapsulation 406. In such embodiments, the outer diameter of the tubular ultrasonic transducer 401 may also be shorted to ground at the encapsulation 406, through a conductive epoxy 408. At least one of the controller 402 or a sensor 405 may also be shorted to ground at the encapsulation 406. In such embodiments, the chassis 407 may provide insulation of the positive terminal of the power storage device 404, and interconnects 403 from ground.

In some embodiments, wherein the implant is made of a metallic material, the encapsulation 406 may be shorted to the implant grounding the internal circuitry of the sensor module.

Figures 4E, 4F:
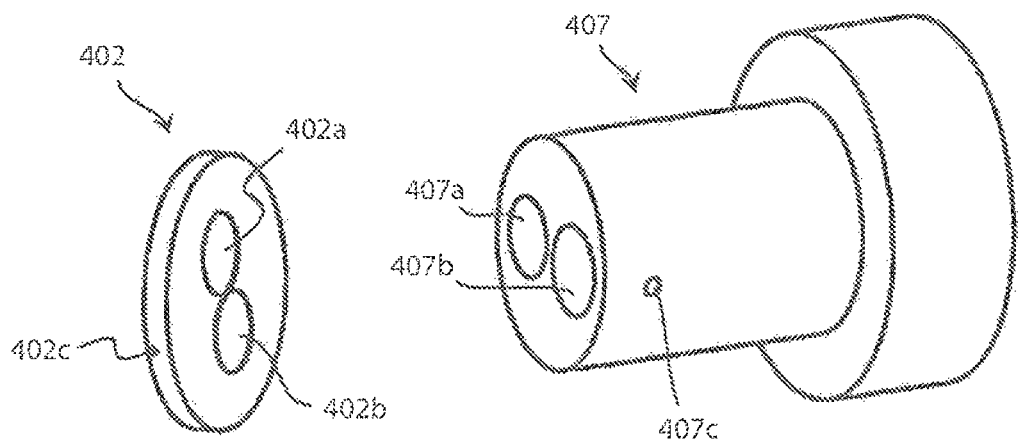
FIG. 4E shows a printed circuit board, configured for three-dimensional stacked circuit integration.
FIG. 4F shows a chassis, the chassis configured for three-dimensional stacked circuit integration.

FIG. 4E shows a controller 402 including small circular printed circuit board having two interconnect terminals 402a, 402b to connect the controller 402 to the power storage device 404 and ultrasonic transducer 401. The controller may include a ground terminal 402c, to ground connect the controller 402 to the encapsulation. In some embodiments, the ground terminal 402c is disposed on the side of the circuit board.

As discussed above, the circuit board may further include other electronic circuitry and components therein including: Analog to Digital Converter (ADC), Digital to Analog Converter (DAC), op-amps, memory and other known electronic components. The controller 402 may be integrated to include a frequency synthesizer (i.e., creates carrier waves for ultrasonic transducer 401), power amplifier and noise filters (i.e., conditions carrier wave), power and read strain gauge (i.e., force sensor controls), and may be configured to adjust carrier waves, power, etc. (such as by computer executable instructions that interface with a user via a graphical user interface, as discussed below).

FIG. 4F shows a chassis 407 configured to receive a tubular ultrasonic transducer 401. The chassis 407 is shown having a first shelf configured to receive and at least partially extend through a tubular ultrasonic transducer 401. The chassis 407 is also shown having two channels 407a, 407b extending axially therethrough. The channels configured to receive at least a portion of an interconnect therein. The chassis 407 is also shown having a connection cavity 407c for connecting one of the interconnects to the ultrasonic transducer 401.

Figure 5A:
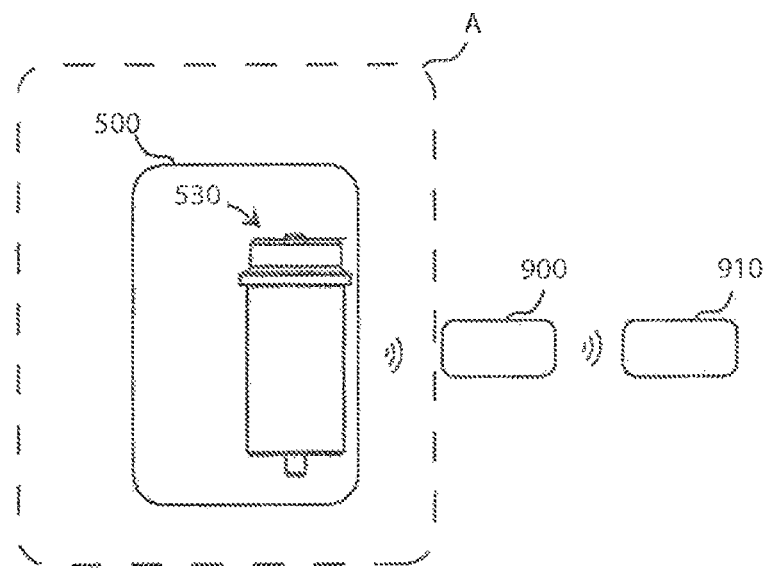
FIG. 5A shows a sensor module in accordance with a second embodiment, the sensor module integrated with an implant disposed within the body of a patient, the sensor module configured to enable the implant transcutaneous bidirectional data communication using an ultrasound signal.

Turning to FIG. 5A, a sensor module 530 is shown integrated with an implant 500 disposed within a body of a patient A, the sensor module 530 enabling the implant 500 with ultrasonic data communication. The sensor module 530 may enable any implant 500 to transcutaneouly transmit and receive data from an external transceiver 900. The data may correspond to one or more of measurements obtained by the sensor module 530, some physical property of the implant 500 and to some physical property of an anatomical item, tissue or structure of the body of the patient A. Additionally, the external transceiver 900 may transmit information to the sensor module 530 and the sensor module 530 may be operably connected to internal circuitry of the implant 500. For example, in some embodiments the external transceiver 900 may transmit adjustment instructions to the sensor module 530 and the sensor module 530 may communicate the adjustment instructions to one or more of a controller and an actuator of an adjustable implant 500.

In some embodiments, the sensor module 530 may be integrated with a processor circuit of an implant using any type of interconnection, cable, or communication protocol including RF, Bluetooth, and ultrasound as described above. The sensor module 530 may receive data from the processor circuit of the implant, and communicate the data transcutaneously to the external transceiver 900.

In some embodiments, the external transceiver 900 may obtain data from the implant 500, for example in the instant embodiment data is obtained via the sensor module 530. The external transceiver 900 may then report the data to a tertiary device 910 via an ultrasonic connection, an RF connection, a cable connection, an internet connection, a cell phone connection, a Wi-Fi connection, a Bluetooth connection, and any known data communication protocol. The tertiary device 910 may be for example: a computer, a cell phone, a server, and any other device capable of data communication. The tertiary device 910 may be enabled to drive the external transceiver 900 to communicate with the sensor module 530, including for example having the capability to actively control an actuator of the implant 500.

Figure 5B:
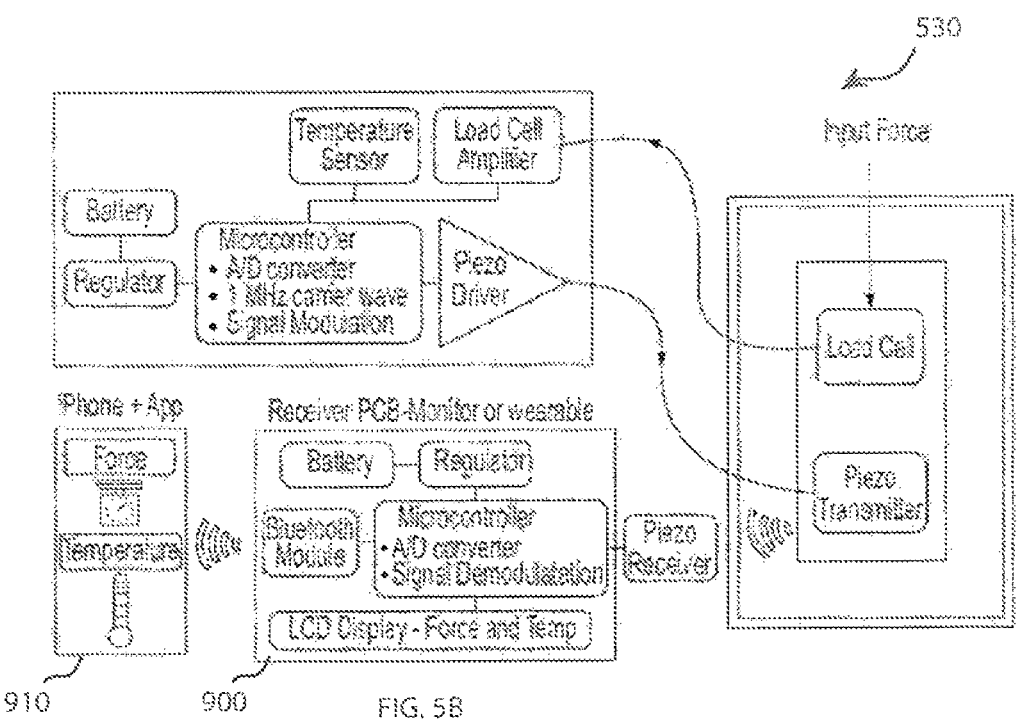
FIG. 5B shows a schematic of implant transcutaneous bidirectional data communication using an ultrasound signal between the sensor module and an external transceiver.

FIG. 5B shows an exemplary schematic of communication between the sensor module 530, the external transceiver 900, and the tertiary device 910. In the instant embodiment the transceiver 900 may be for example a piece of wearable technology, and the tertiary device 910 may be for example a cell phone.

The external transceiver 900 may include an external adjustment device configured to for adjusting an adjustable implant. The external adjustment device may include one or more ultrasonic transducer disposed on a surface of the external adjustment device. Upon placing the external adjustment device in close proximity to a patient's skin, a bidirectional ultrasound communication link or network may be established between the external adjustment device and one or more implants configured for ultrasound communication. The bidirectional ultrasound communication link established to pass distraction and or hi oin formation between the external transceiver 900 and the one or more implants.

In some embodiments, the external transceiver 900 may be a wearable device. The wearable device may be for example: a bracelet, a watch, an arm band, arm sleeve, arm brace, a leg band, a leg sleeve, a leg brace, a back brace, a body sleeve, a neck brace, a head brace, and any type of other wearable device known and used in the art. The wearable device may be made using additive manufacturing techniques including 3D printing.

The external transceiver may include a ultrasonic transducer, or multiple ultrasonic transducers forming one or more array. A one dimensional array has multiple ultrasonic transducers disposed in a column. The ultrasonic transducer of a one dimensional array can be assigned a position relative to their position on the array. A two dimensional array has multiple ultrasonic transducers disposed in a matrix or pattern. The ultrasonic transducer can be assigned a location relative to two dimensions of the matrix.

Now, the external transceiver 900 communicates with the sensor module 530 using transcutaneous bidirectional ultrasound signals transmitted from an ultrasound transducer 501 to the external transceiver 900, and from the external transceiver 900 to the ultrasound transducer 501. In this embodiment, the ultrasound transducer 501 includes a piezoelectric transducer.

The external transceiver 900 may communicate with the tertiary device 910. In some embodiments the tertiary device 910 may communicate with one or more of the external transceiver 900 and the sensor module 530 using ultrasound signals. In some embodiments, the tertiary device 910 may communicate with the external transceiver 900 using for example RF communication protocols. The tertiary device 910 may be in further communication with one or more of the internet and other telecommunication networks, allowing a user to remotely access the sensor module 530, and even control an implant 500 from anywhere.

In some embodiments, a High-intensity focused ultrasound (HIFU) ultrasonic transducer having a fixed focal depth may be provided to one or more of the external transceiver and the sensor module to provide enhanced reception capabilities to the sensor module or the external transceiver. An offset, including an adjustable offset, may be provided to the external transceiver to move the external transceiver to and hold the external transceiver at a distance from the sensor module corresponding to the fixed focal depth of the HIFU ultrasonic transducer. This allows a user to find a maximum amount of transmission to or from the sensor module and improves power transmission and data communication between the sensor module and the external transceiver.

Figure 5C:
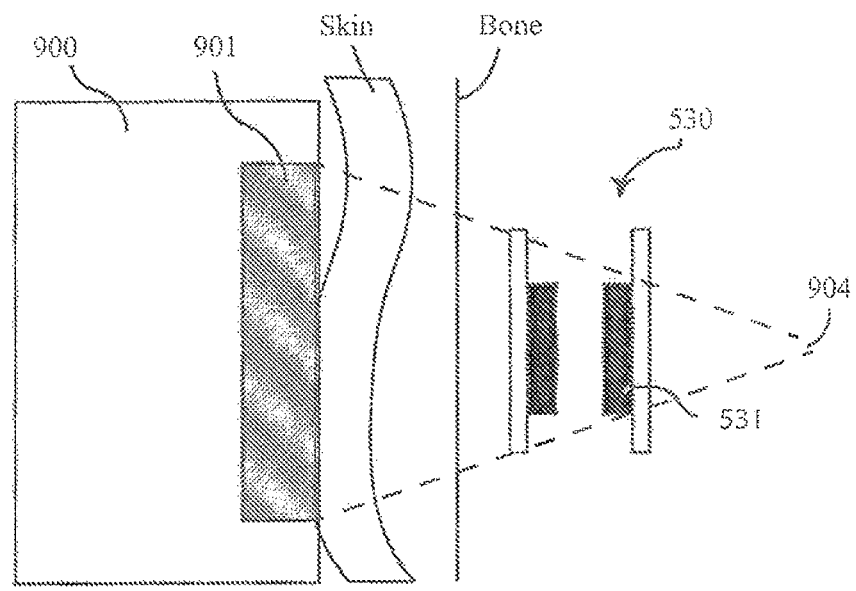
FIG. 5C shows an external transceiver configured for transcutaneous bidirectional data communication using an ultrasound signal, communicating with the sensor module.

FIG. 5C shows an external transceiver 900 including a High-intensity focused ultrasound (HIFU) ultrasonic transducer 901 having a fixed focal depth 904, the ultrasonic transducer configured to communicate with the sensor module 530. The ultrasound signals transmitted by the external transceiver 900 are focused to the focal depth 904 which may provide improved transcutaneous transmission of ultrasound signal as compared with a non-focused ultrasound signal.

However, as one with skill in the art may appreciate, improper alignment of focal depth 904 of the HIFU ultrasonic transducer 901 to the skin may induce air-gaps between the skin of the patient and the HIFU ultrasonic transducer 901. These air gaps can result in high impedance to the ultrasound signal, reducing transmission to the sensor module 530 disposed within the body of the patient. Further because the focal depth 904 is fixed, some of the ultrasound signal will miss the ultrasonic transducer 531 of the sensor module 530. This may result in for example less power being communicated to the sensor module 530.

Figure 5D:
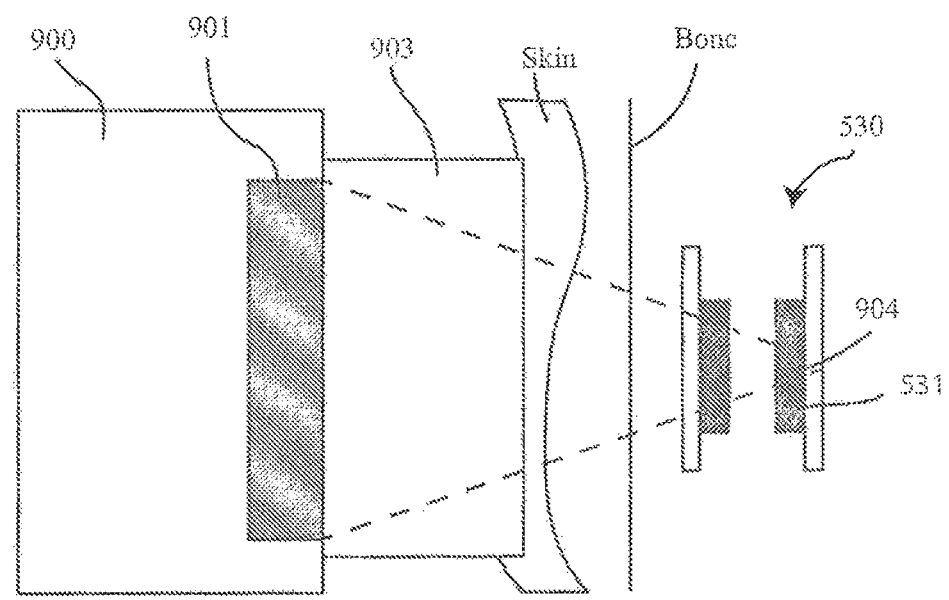
FIG. 5D shows an external transceiver configured for transcutaneous bidirectional data communication using an ultrasound signal, including a standoff.

FIG. 5D shows the external transceiver 901 configured for transcutaneous bidirectional data communication using an ultrasound signal, including a standoff 903. The standoff 903 may be made out of and include a gel material having favorable ultrasound transmission characteristics. At least a portion of the standoff 903, may be malleable and configured to conform to curvature of a patient's skin. The standoff 903 is configured to form to the skin of the patient, provide an air tight connection to the skin, and minimize the air-gaps between the HIFU ultrasound transducer 901 and the skin of the patient. Further, the standoff 903 may be adjustable in depth, allowing a user to change an amount of displacement between the external transceiver 900 and the skin of the patient, and thereby allowing a user to change an amount of displacement between the ultrasonic transducer 901 and the sensor module 530. Allowing the user to change the amount of displacement allows the user to move the external transceiver 900 relative to the sensor module 530, such that the user can actively adjust and optimize an amount of signal transmitted to the sensor module 530.

As one with skill in the art may appreciate, the amount of transmission observed at the sensor module 530 in FIG. 5D will be greater than the amount of transmission observed at the sensor module in FIG. 5C. This is because the standoff 903 allows the user to align the focal depth 904 to the sensor module 530. The bidirectional ultrasonic data communication link between the sensor module 530 and the external transceiver 900 may be used to give live-feedback and enable the user to search for a maximum amount of transmission.

Figure 6A:
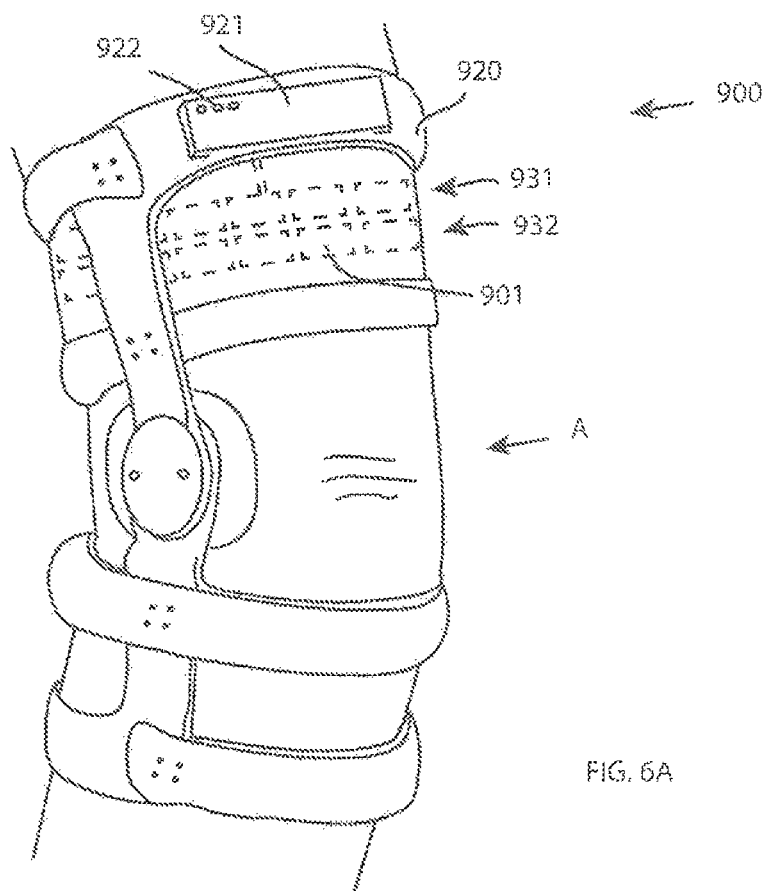
FIG. 6A shows an embodiment of an external transceiver configured for transcutaneous bidirectional data communication using an ultrasound signal, the external transceiver including a knee brace.

FIG. 6A shows an embodiment of an external transceiver 900 configured for ultrasonic communication including a knee brace 920. In this embodiment, the external transceiver 900 includes a controller 902 and one or more LED display indicators 922. The one or more LED display indicators 922 may indicate to a user a status of the device.

The external transceiver 900 may include any number of ultrasonic transducers 901 or ultrasonic transducer arrays 931.

In some embodiments the external transceiver 900 may include a display. The display may be a programmable touch screen display. For example, LED, LCD, or plasma display.

A first user, for example a physician, may program the external transceiver 900 or a controller 902 of the external transceiver 900 with a first set of operational instructions. The external transceiver 900 may be programmed such that these operational instructions may be password protected. In some embodiments, the first user may be able to access the device remotely through for example the internet. The first user may send operational instructions to the external transceiver 900 over a remote connection. The first user may also download from the external transceiver 900, data regarding measurements obtained by the external transceiver 900.

A second user may be able to operate the external transceiver 900 through their cell phone, a computer, any other tertiary device 910, or the display. The second user may be able to program the device with a second set of operational instructions. The second user may be able to pair a tertiary device 910 to the external transceiver 900.

The external transceiver 900 of FIG. 6A includes two arrays of ultrasonic transducers 931, 932 extending around at least a portion of the patient A. The array includes a plurality of ultrasonic transducers 901. The ultrasonic transducers 901 are disposed on an inner surface of the knee brace such that they are in close proximity to the patient A's skin when the patient A wears the knee brace. In FIG. 6A the array of ultrasonic transducers 931, 932 extends around the patient A's leg, encircling at least a portion the patient A's leg, and a femur therein. As one with skill in the art can appreciate the external transceiver 900 may include any wearable medium including a leg brace 920, an arm brace, a neck brace, a head brace, an arm sleeve, a leg sleeve, and any other wearable article as discussed above.

Figure 6B:
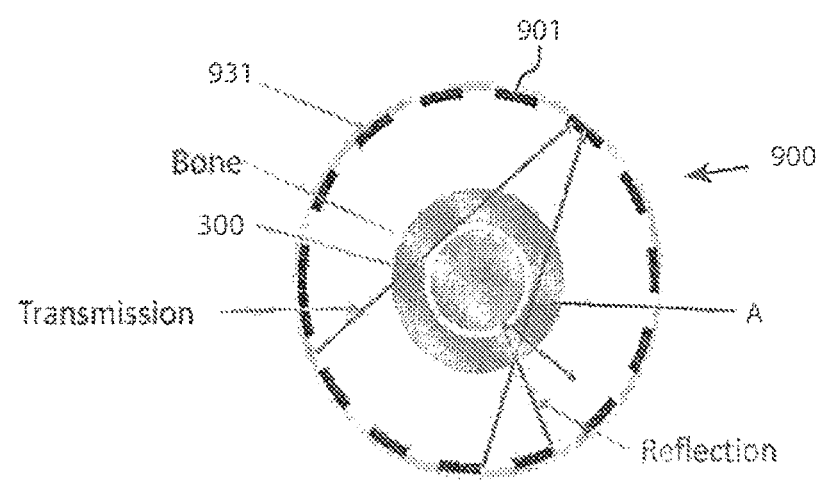
FIG. 6B shows a cross-sectional view of the external transceiver being worn by a patient having an intramedullary implant disposed within a bone.

FIG. 6B shows a cross-sectional view of the external transceiver 900, the external transceiver worn by a patient having an implant 300 disposed inside their body. In this example, the external transceiver 900 may be the same external transceiver 900 as FIG. 6A. The implant 300 may be disposed in the patient A's body. In this example, the implant 300 may be in the patient's femur.

As discussed above the external transceiver 900 may be configured to communicate with the implant using ultrasound waves. For example, the array of ultrasonic transducers 931 may transmit a particular step function of ultrasound waves to the implant 300. The implant 300 may include an ultrasonic transducer 301 configured to receive the ultrasound waves and convert them to electrical energy. The implant 300 may use the electrical energy to power the implant 300. The implant 300 may be an adjustable implant and may use the electrical energy to activate an actuator of the implant 300, for example an electric motor to change a dimension of the implant 300. The implant 300 may use the electrical energy to activate a controller 302 of the implant 300. The controller 302 of the implant 300 may communicate with the controller of the external device 900. The controller 302 may establish a connection to the internet, or to a tertiary device 910 through the external transceiver 900. The implant 300 may include a sensor 305 configured to sense a measurement of the implant 300 or surrounding tissues or fluids. The implant 300 may communicate sensor measurements to the external transceiver 900 using ultrasound waves. One or more of the external transceiver and the implant may include some of the various components and functionalities as discussed throughout this disclosure.

In some embodiments the external transceiver 900 may image or detect a location of the implant 300 by detecting an amount of transmission or an amount of reflection of ultrasound waves. In some embodiments the external transceiver 900 may form one or more ultrasound images of the bone and or implant 300 using ultrasound waves.

In some embodiments to form a three dimensional image, the external transceiver 900 may yield bone densities in four or more quadrants of a bone. In some embodiments: ultrasound waves may be generated by one ultrasonic transducer 901 of the array of ultrasonic transducers 931, the ultrasound waves emitted by the one ultrasonic transducer 901 may act analogously to a light source in a camera. The rest of the ultrasonic transducers 901 will detect the reflection and/or transmission of the ultrasound waves, the array 931 acting analogously to the focal plane array of a camera. This sequence may repeat one element at a time around the array. The controller 902 or some tertiary device 910 may process the data obtained by the ultrasonic transducers to form a stereoscopic three dimensional image looking at the subject from multiple perspectives.

Figure 7:
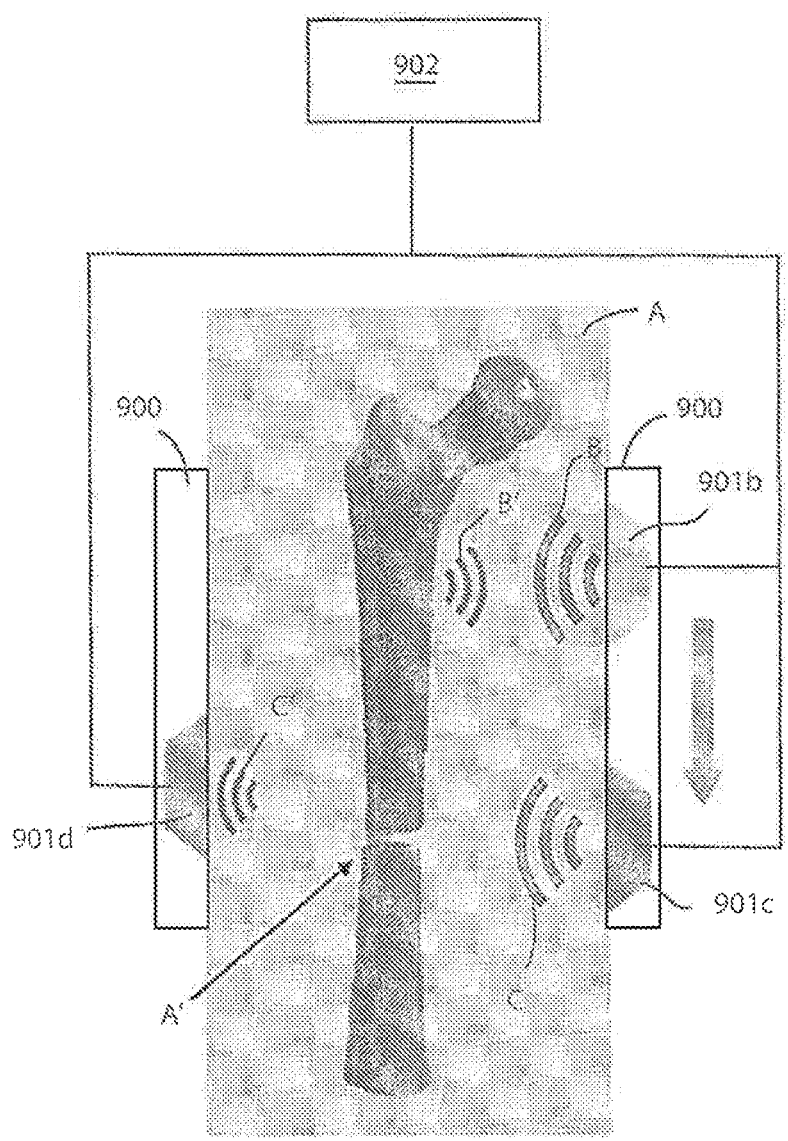
FIG. 7 shows a diagram of the external transceiver determining a location of low bone density and transmitting ultrasound waves modulated at a healing frequency to the location.

FIG. 7 shows a diagram of an external transceiver 900 having at least three ultrasonic transducers 901b, 901c, 901d configured to transmit ultrasound waves. The first ultrasonic transducer 901b may be part of a first array 931, the second and third ultrasonic transducers 901c, 901d may be part of a second array 932, the array extending around at least a portion of the patient A's leg.

The external transceiver 900 is shown including a controller 902, operably connected to the ultrasonic transducers 901b, 901c, 901d. In some embodiments the external transceiver 900 may include one or more of a memory module for storing data obtained by the ultrasonic transducers 901b, 901c, 901d, a networking device for transferring the data to a tertiary device, and a power storage device operably coupled to the controller.

The external transceiver 900 is configured to noninvasively detect a location corresponding to a position of low bone density A' on a bone of the patient A. The external transceiver 900 may also be configured to generate a three dimensional plot of bone density. For example, the controller may assign known locations along a length of the external transceiver 900, to the ultrasonic transducer 901b, 901c, 901d or to the array of ultrasonic transducers disposed on the external transceiver 900.

The controller will instruct a first ultrasonic transducer 901b, or a first array of ultrasonic transducers, to emit ultrasound waves at a chosen frequency B. One or more of the ultrasonic transducers 901b, 901c, 901d may then be instructed to sense the ultrasound waves B of the first ultrasonic transducer 901b.

In areas of relatively high bone density, there will be a relatively strong reflection of the ultrasound waves by the bone. In areas of relatively low bone density, elevated transmission rates of ultrasound waves across the bone will be observed.

In the illustrated embodiment, relatively high amounts of reflection will be observed by the first ultrasonic transducer 901b and the controller will assign high bone density to the position correlated with the position of the first ultrasonic transducer 901b or to the region associated with the array assigned to the first ultrasonic transducer 901b. The controller may instruct a second ultrasonic transducer 901c to transmit ultrasound waves at a chosen frequency C. The ultrasound waves C' will pass through the area of low bone density A' and will be observed by a third ultrasonic transducer 901d for example on the other side of the bone. The controller will assign a low bone density to the position correlated with the position of the second ultrasonic transducer 901c or to a region associated with an array assigned to the second ultrasonic transducer 901c. The controller can then construct a plot of bone density along the length of the external transceiver 900.

In some embodiments, the external transceiver 900 is configured to locate a position of low bone density A' on a bone of the patient A, and wherein upon determining the location, the controller is configured to instruct one or more of the ultrasonic transducers 901b, 901c, 901d to transmit ultrasound waves at a therapeutic ultrasonic frequency to promote bone healing or bone growth. Studies have correlated certain ultrasonic frequencies to improved bone healing and therapy.

The position of low bone density A' may be determined by the external transceiver 900 as described above. However, in some embodiments the position of low bone density may be acquired by inputting the location into the external transceiver 900 using for example a touch screen LCD display operably coupled to the controller. In some embodiments, the position of low bone density may be acquired by inputting the location into the external transceiver 900 remotely from a tertiary device 910 using an established radiofrequency connection, for example a Wi-Fi or a Bluetooth connection. In some embodiments, the external transceiver 900 may be in communication with one or more implants within the patient via ultrasound waves and the one or more implants may determine the location of bone density and communicate that position to the external transceiver 900.

Knowing the position of low bone density A', the controller 902 may be preprogrammed or remotely programmed with treatment instructions. The controller 902 may then instruct one or more of the ultrasonic transducers to transmit ultrasound waves at a bone healing frequency to the position.

For example, in FIG. 7 the controller 902 of the external transceiver 900 may drive the second ultrasonic transducer 901c and the third ultrasonic transducer 901d to transmit ultrasound waves at a specific healing frequency. The healing frequency may be the same or different than the frequency chosen to determine the location of low bone density. Also, the second ultrasonic transducer 901c and the third ultrasonic transducer 901d may be part of an array, in which case the controller 902 may instruct the ultrasonic transducers of that array to transmit ultrasound waves at the bone healing frequency to the location of low bone density A'.

Figure 8:
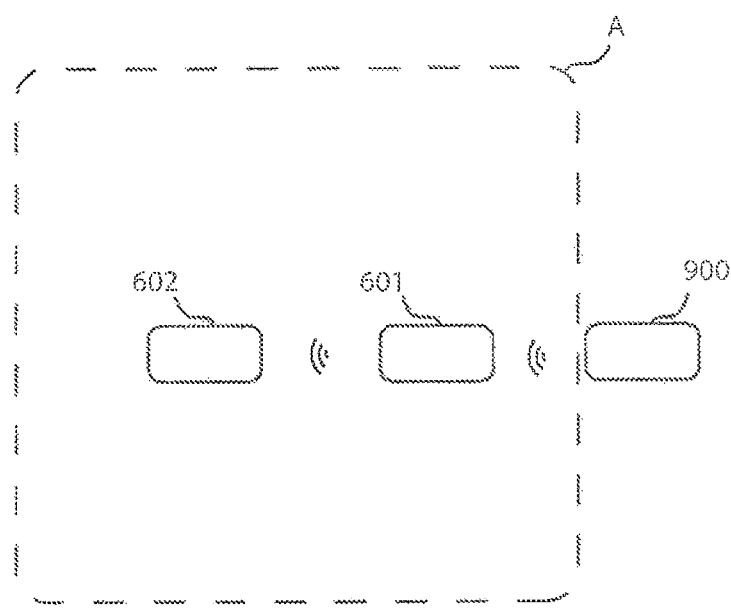
FIG. 8 shows an exemplary Body Area Network established between two implants and an external transceiver, with the Body Area Network established using ultrasound waves.

FIG. 8 shows a first implant 601 in communication with a second implant 602 within the body of a patient A, the communication established using ultrasound waves. Communication between two or more of the implants or the external transceiver 900 may establish a Body Area Network (BAN). In some embodiments, an ad hoc mesh network may be established across the implants using ultrasound signals.

As discussed above, the implant may include a sensor module, or have an ultrasonic data communication circuit integrated into the implant.

Figure 9A:
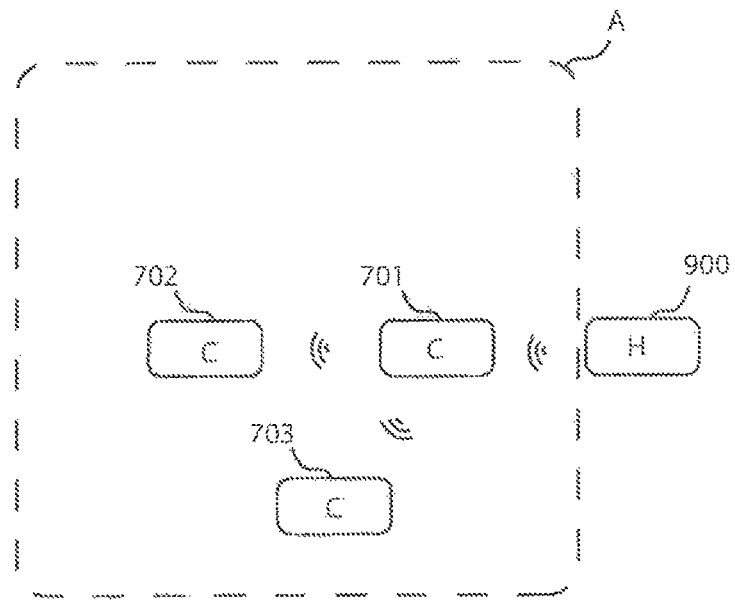
FIG. 9A shows an exemplary Body Area Network established between three implants located inside a body of a patient and an external transceiver.

Turning to FIG. 9A, in some embodiments, a Body Area Network may be established having an external transceiver 900 assigned a host status, and one or more implants 701, 702, 703 assigned a client status.

Figure 9B:
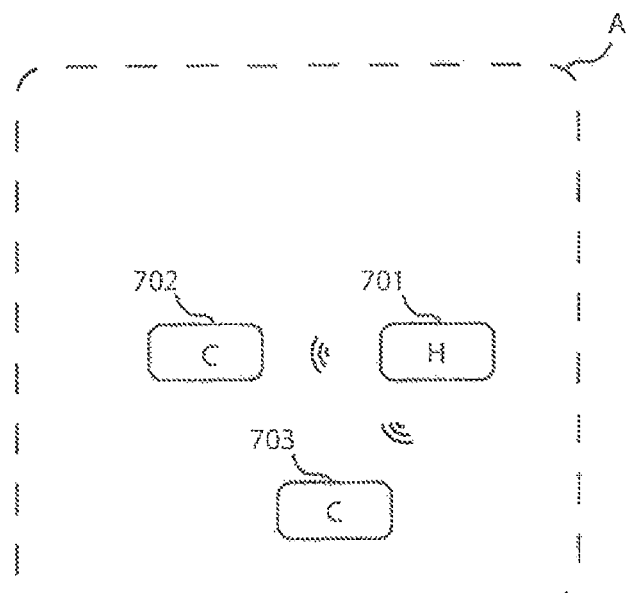
FIG. 9B shows an exemplary Body Area Network established between three implants located inside a body of a patient wherein one of the implants has been designated host status.

As seen in FIG. 9B, in some embodiments, the network may be programmed such that upon a disconnection of the host from the network, a new host will be chosen between the remaining clients. The host status may be transferred around the network as the implants activate and deactivate.

The Body Area Network connection may provide the host access to drive the client implants. This includes one or more of: powering the client implant, activating the client implant, actuating the client implant, receiving data from the client implant, and adjusting the client implant in any way as discussed supra or commonly known in the art.

The Body Area Network may establish through the host a connection to any external network. For example, in FIG. 9A if the host external transceiver 900 is configured to connect to an external network, the host will provide access to the clients across said network. Similarly, in FIG. 9B if the host implant 701 is configured to connect to an external network, the host will provide access to the clients across said network. This allows the hosts and clients alike to be controlled, observed, and accessed remotely. In some embodiments the firmware of the host and clients may be updated remotely using this connection.

As one with skill in the art may appreciate, these exemplary embodiments are not intended to be exhaustive. The structure and features of the individual embodiments may be interchangeable between the other various embodiments. Wherein a specific feature of one embodiment is not explicitly stated as part of another, this disclosure is intended to include variations, with features of the embodiment intended to be communicable to other embodiments to arrive at the full and reasonable scope of the claims.

FIGS. 10-16 represent flow diagrams of exemplary methods of transcutaneous transmission of power and/or data between one or more implant using an ultrasound signal, in accordance with at least some of the embodiment as described herein. Although the blocks in the figure are illustrated in a sequential order, the blocks may in some instances be performed in parallel, and/or in a different order than those described therein. Also, the various blocks may be combined into fewer blocks, divided into additional blocks, and/or removed based upon the desired implementation.

In addition, the blocks in the figure may show functionality and operation of one possible implementation of the present embodiment. In this regard, the block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, the blocks in the figure may represent circuitry that is wired to perform the specific logical functions in the process. Illustrative methods, such as those shown in the blocks in the figure, may be carried out in part by a component or components on the internet, in the cloud and/or on a computer system. However, it should be understood that the example methods may instead be carried out by other entities or combinations of entities (i.e., by other computing devices and/or combination of computer devices), without departing from the scope of this disclosure. For example, functions of the method of the blocks in the figure may be fully performed by a computing device (or components of a computing device such as one or more processors), or may be distributed across multiple components of the computing device, across multiple computing devices (e.g., control unit and image processing device), and/or across a server.

Figure 10:
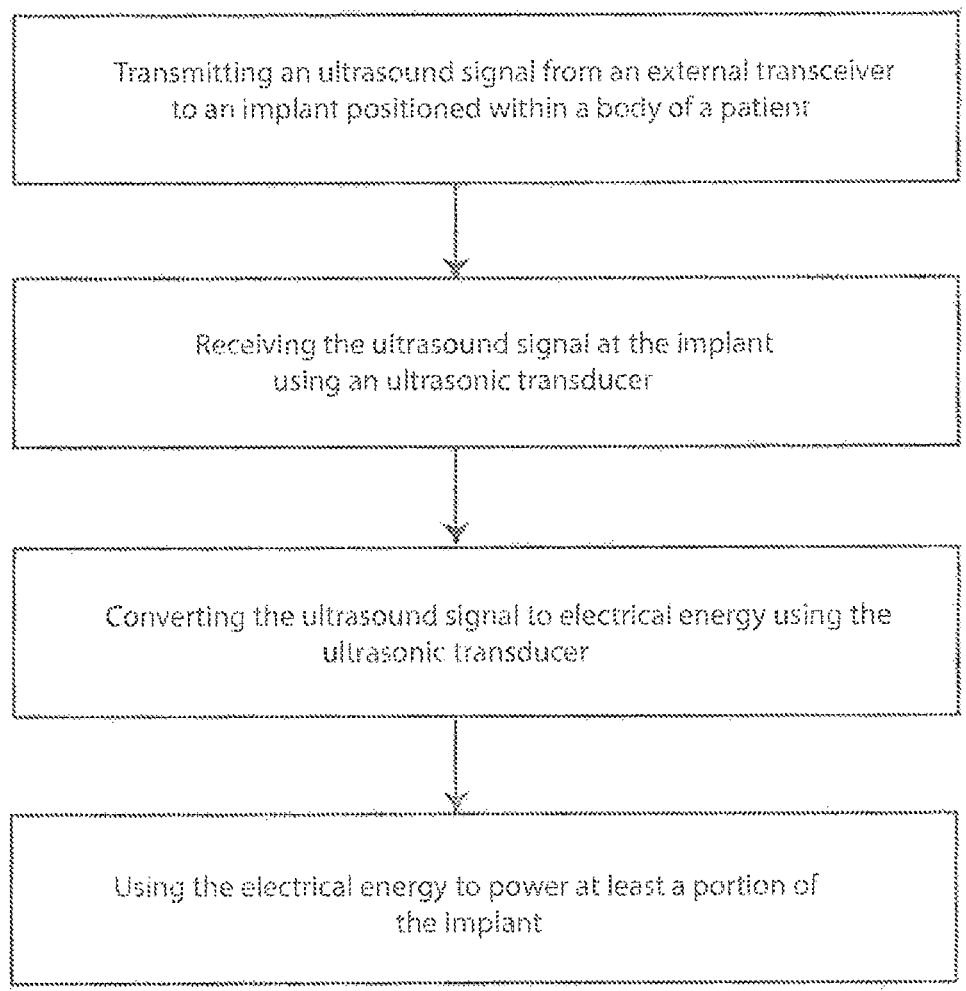
FIG. 10 shows an exemplary method of powering an implant using ultrasound waves.

Now, the exemplary method shown in FIG. 10 provides an exemplary method of transcutaneous power transmission using ultrasound waves, the method including the steps: transmitting an ultrasound signal from an external transceiver to an implant positioned within a body of a patient, receiving the ultrasound signal at the implant using an ultrasonic transducer; converting the ultrasound signal to electrical energy using the ultrasonic transducer; and using the electrical energy to power at least a portion of the implant.

As discussed above, powering the implant may include activating the implant, actuating the implant, charging the implant, or any other form of supplying power to internal circuitry of the implant. The electrical energy may be immediately or subsequently used. Further, the implant may have an ultrasonic transducer, and as described above may include a sensor module.

Figure 11:
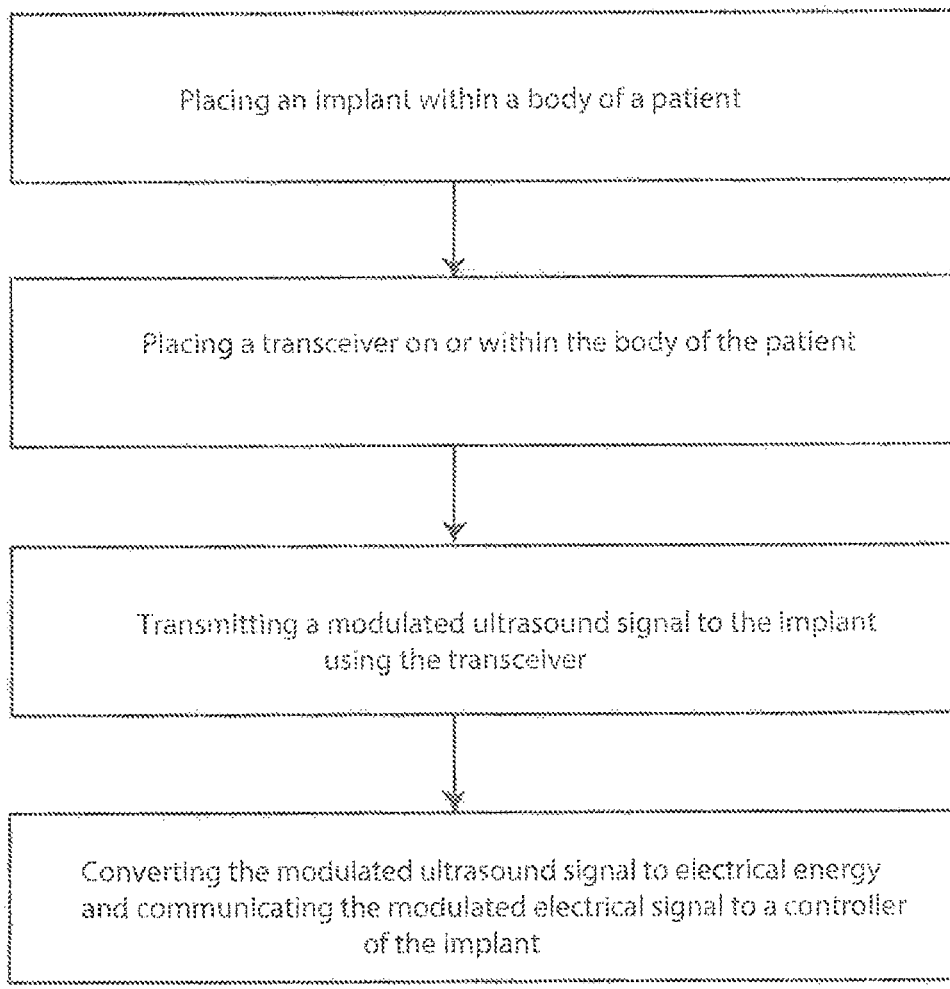
FIG. 11 shows an exemplary method of transcutaneous data transmission using ultrasound waves.

FIG. 11 provides an exemplary method of transcutaneous signal transmission using ultrasound waves, the method including: placing an implant within a body of a patient, placing a transceiver on or within the body of the patient, transmitting a modulated ultrasound signal to the implant using the transceiver, and converting the modulated ultrasound signal to electrical energy and communicating the modulated electrical signal to a controller of the implant.

Figure 12:
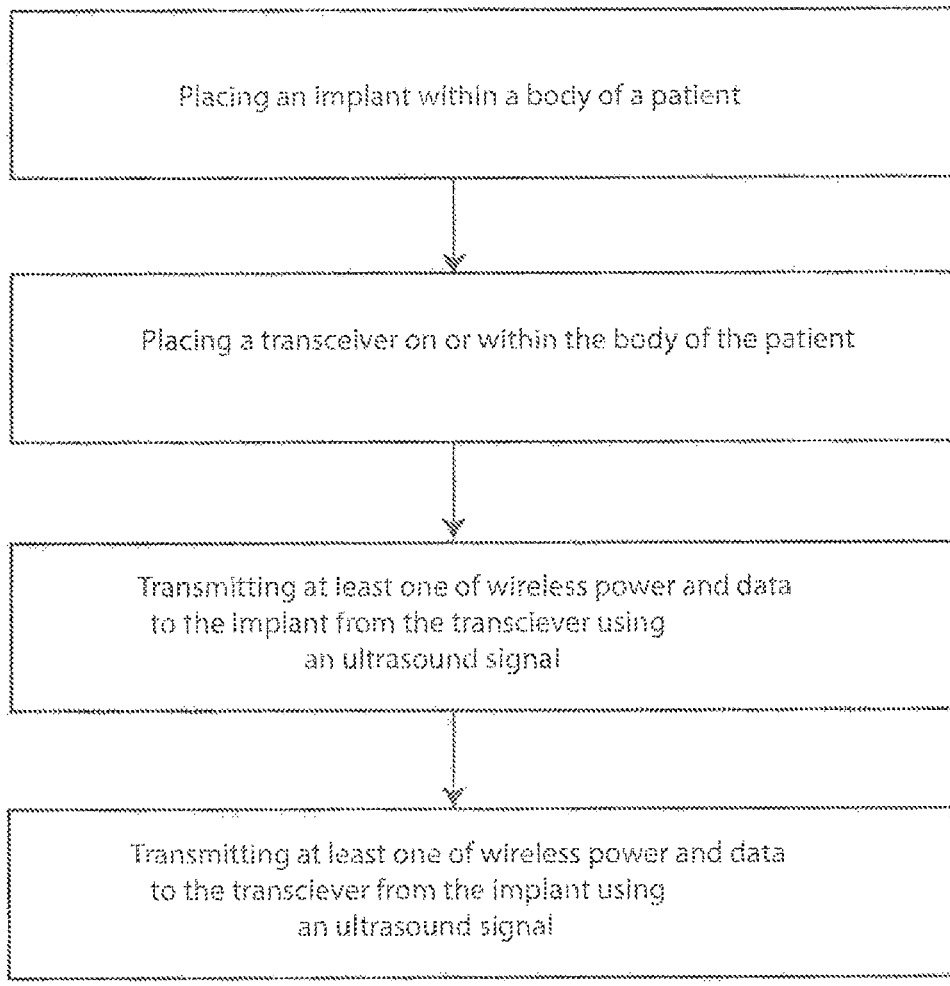
FIG. 12 shows an exemplary method of transcutaneous power and/or data transmission using ultrasound waves.

FIG. 12 provides an exemplary method of transcutaneous bidirectional data transmission using an ultrasound signal, the method including: placing an implant within a body of a patient, transmitting at least one of wireless power or data to the implant from the transceiver using an ultrasound signal, and transmitting at least one of wireless power or data to the transceiver from the implant using an ultrasound signal.

Figure 13:
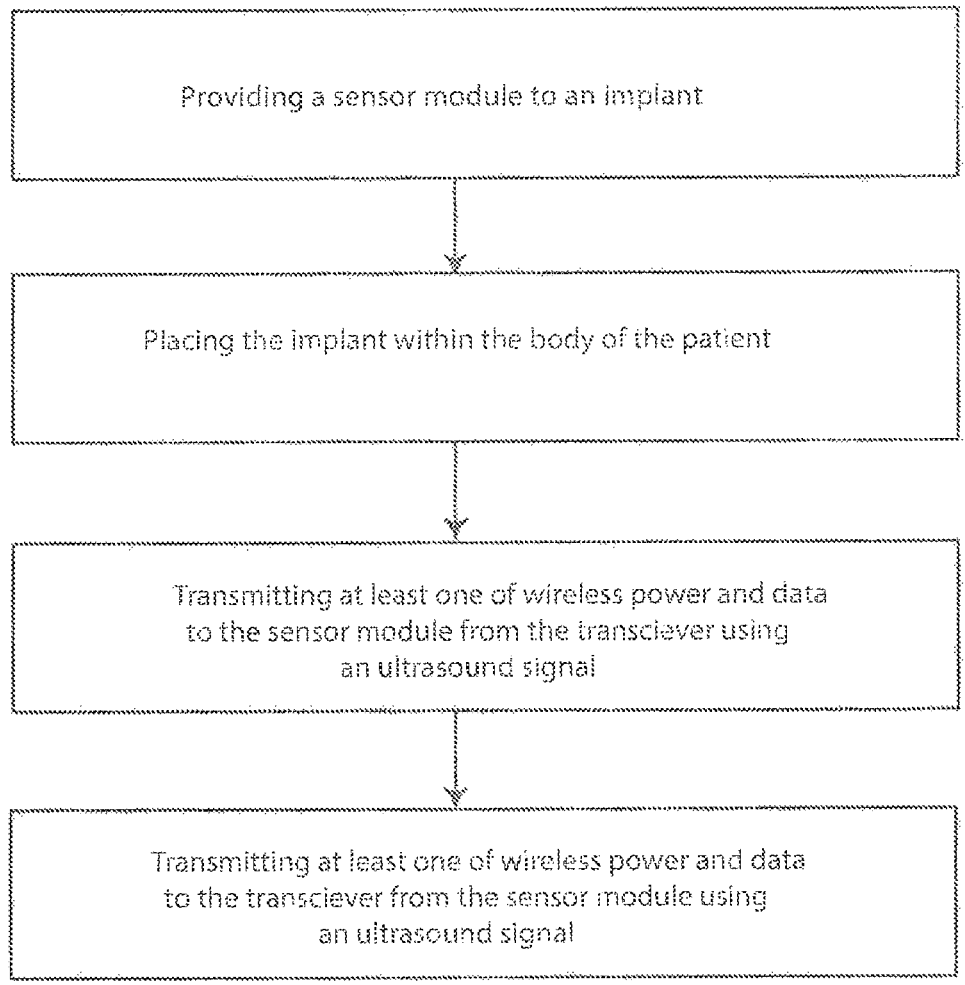
FIG. 13 shows an exemplary method of using a sensor module.

FIG. 13 provides an exemplary method of transcutaneous bidirectional data transmission using ultrasound waves, the method comprising the steps of: providing a sensor module to an implant, placing the implant within a body of a patient, transcutaneously transmitting at least one of wireless power or data to the sensor module from the transceiver using an ultrasound signal, and transmitting at least one of wireless power or data to the transceiver from the sensor module using an ultrasound signal.

In some embodiments the method may further include the step of communicating information received by the sensor module to a controller of the implant. In some embodiments this step may be performed through a direct connection, for example a wired connection. In some embodiments this step may be performed through an indirect connection, for example a wireless connection including one or more of RF communication and ultrasound communication.

Figure 14:
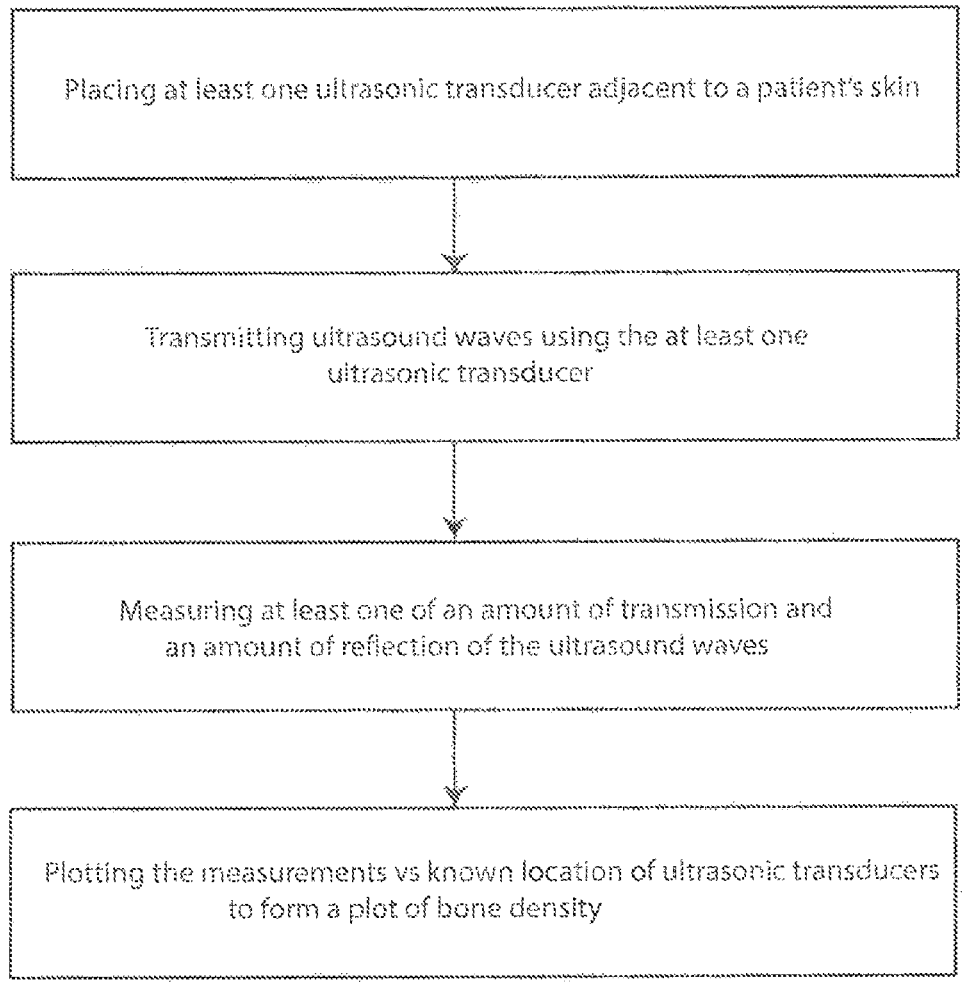
FIG. 14 shows an exemplary method for a plotting bone density.

FIG. 14 provides an exemplary method for a plotting bone density including: placing at least one ultrasonic transducer adjacent to a patient's skin, transmitting ultrasound waves using the at least one ultrasonic transducer; measuring at least one of an amount of transmission or an amount of reflection of the ultrasound waves, plotting the measurements vs the known location of the ultrasonic transducers to form a plot of bone density.

Figure 15:
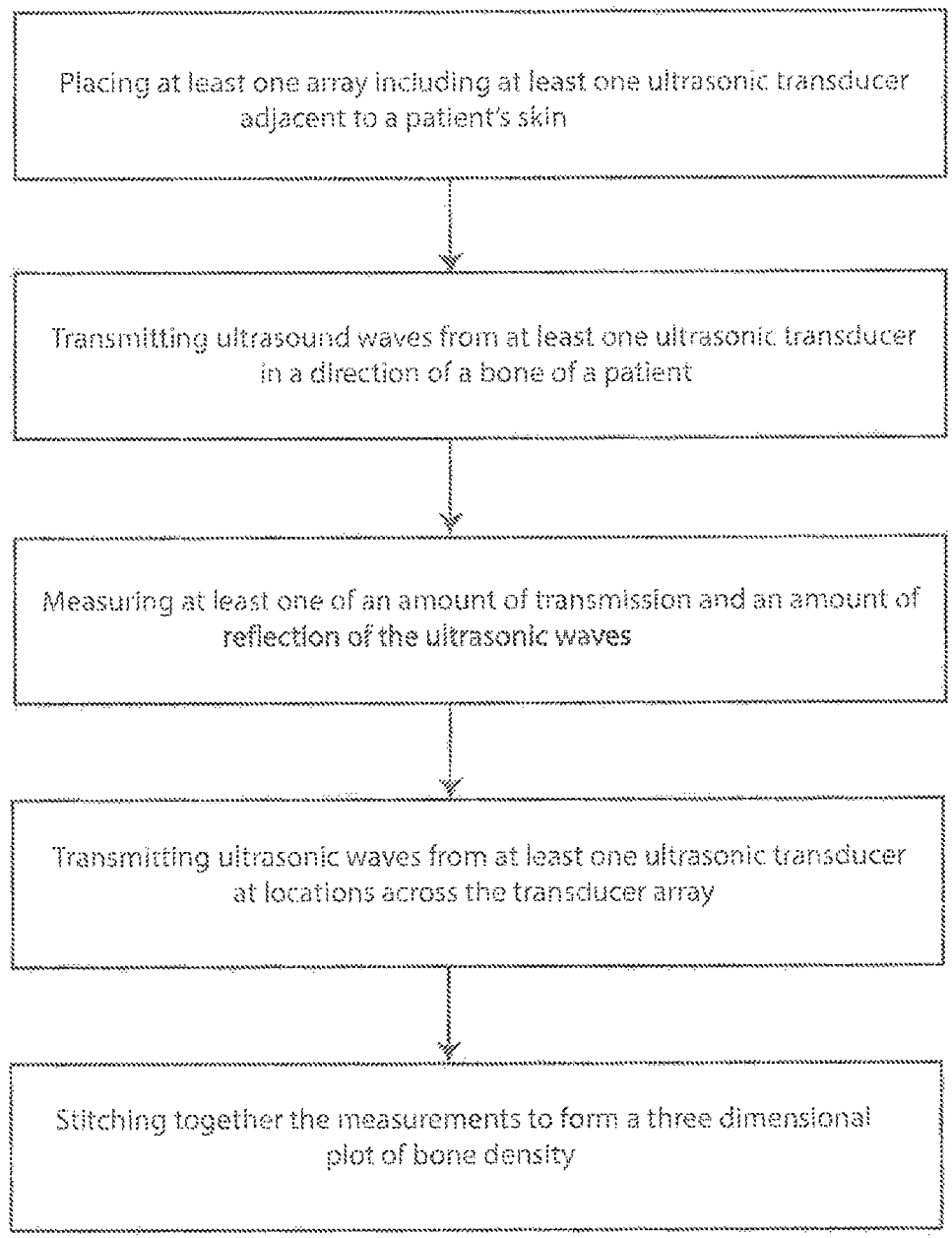
FIG. 15 shows an exemplary method for three-dimensional bone density imaging.

FIG. 15 provides an exemplary method for three-dimensional bone density imaging including: placing at least one array including at least one ultrasonic transducer adjacent to a patient's skin, transmitting ultrasound waves from at least one ultrasonic transducer in a direction of a bone of a patient, measuring at least one of an amount of transmission or an amount of reflection of the ultrasound waves, transmitting ultrasound waves from at least one ultrasonic transducer at locations across the transducer array; stitching together the measurements to form a three dimensional plot of bone density.

Figure 16:
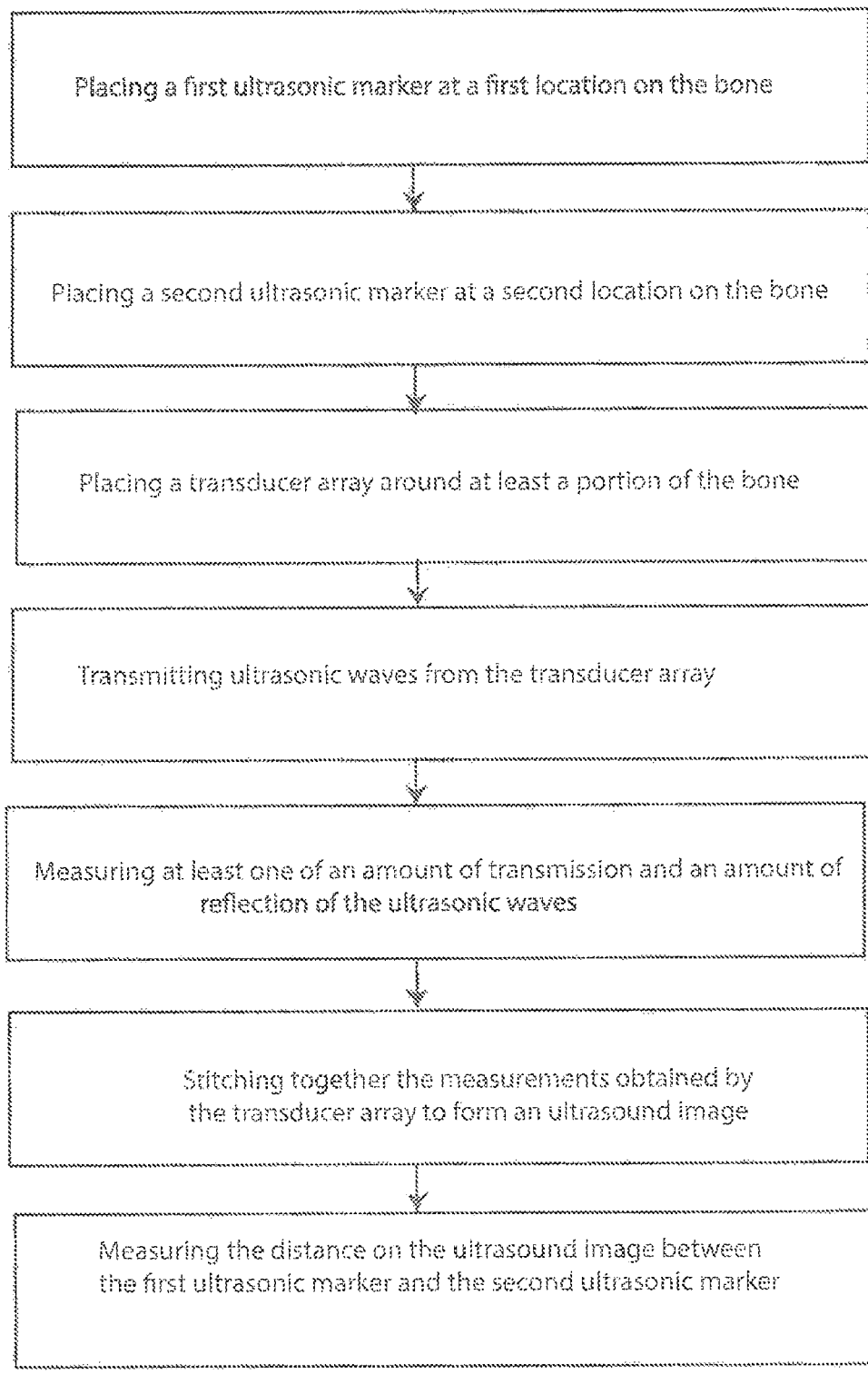
FIG. 16 shows an exemplary method for measuring an increase in length of a bone.

FIG. 16 provides an exemplary method for measuring an increase in length of a bone including: placing a first ultrasonic marker on a first location on the bone, placing a second ultrasonic marker on a second location on the bone, placing a transducer array around at least a portion of the bone, the transducer array comprising at least one ultrasonic transducer; transmitting ultrasound waves from the at least one ultrasonic transducer; measuring at least one of an amount of transmission or an amount of reflection observed by the ultrasonic transducer at the location on the transducer array; stitching together the measurements obtained by the transducer array to form an ultrasound image; measuring the distance on the ultrasound image between the first ultrasonic marker and the second ultrasonic marker.

As one with skill in the art can appreciate, these exemplary embodiments of methods are not intended to be exhaustive. The blocks of the individual methods may be substituted and interchangeable between the various embodiments. Additional blocks may be added and substituted to the various embodiments corresponding to additional steps and features disclosed throughout these papers.

Now, although particular features and embodiments have been described in an effort to enable those with skill in the art to make and use the claimed invention, it should be understood that several variations, alterations or substitutions can be achieved to arrive at the subject matter disclosed. Nothing in this description shall be construed as limiting the spirit and scope of the invention as set forth in the appended claims, below.

What is claimed is:

1. An apparatus comprising:
a sensor module comprising:
an encapsulation hermetically sealing the sensor module;
an ultrasonic transducer;
a power store;
one or more sensors;
a controller operatively coupled to the ultrasonic transducer and the one or more sensors; and
a charging circuit operably connected to the power storage device and the ultrasonic transducer such that the power storage device receives power from the ultrasonic transducer; and an implantable medical device having an interior portion, wherein at least a portion of the sensor module is disposed within the interior portion of the implantable medical device,
wherein the controller is configured such that upon receipt of ultrasound waves at the ultrasonic transducer corresponding to a particular modulated signal, the controller modifies an electrical switch to cause powering or powering down of the implantable medical device.

2. The apparatus of claim 1, wherein at least a portion of the sensor module is disposed at an exterior portion of the implantable medical device.

3. The apparatus of claim 1, wherein the ultrasonic transducer is a tubular piezoelectric transducer configured to transmit and receive ultrasound signals.

4. The apparatus of claim 1, wherein the particular modulated signal has a particular step function of particular temperance.

5. The apparatus of claim 1, wherein the ultrasonic transducer is configured to transmit data through at least four inches of water at a rate of at least 5 values per second with a data reliability of at least 95%.

6. The apparatus of claim 1,
wherein the implantable medical device is a spinal medical device;
wherein the implantable medical device is an intramedullary implant configured to be disposed within a bone; or
wherein the one or more sensors include at least one sensor selected from the group consisting of: a force sensor, a temperature sensor, a pressure sensor, a capacitance sensor, a resistance sensor.

7. The apparatus of claim 1, wherein the one or more sensors include a force sensor operably coupled to the implantable medical device using an adapter plate.

8. The apparatus of claim 1, wherein the ultrasonic transducer, power store, and controller are stacked and connected via interconnects.

9. The apparatus of claim 1, wherein the power store has a ground terminal shorted to the encapsulation.

10. The apparatus of claim 1, wherein an outer surface of the ultrasonic transducer is shorted to the encapsulation through a conductive epoxy.

11. The apparatus of claim 1, wherein the controller is shorted to ground at the encapsulation.

12. The apparatus of claim 1, wherein the sensor module comprises a chassis providing insulation of a positive terminal of the power store.

13. The apparatus of claim 1, wherein the encapsulation is shorted to the implantable medical device.

14. A system comprising:
a host device,
first and second sensor modules, each comprising:
an encapsulation hermetically sealing the respective sensor module;
an ultrasonic transducer;
a power store;
one or more sensors;
a controller operatively coupled to the ultrasonic transducer and the one or more sensors; and
a charging circuit operably connected to the power storage device and the ultrasonic transducer such that the power storage device receives power from the ultrasonic transducer;
a first implantable medical device having a first interior portion, wherein at least a portion of the first sensor module is disposed within the first interior portion; and a second implantable medical device having a second interior portion, wherein at least a portion of the second sensor module is disposed within the second interior portion, wherein the first and second sensor modules are configured to communicate between each other using respective ultrasonic transducers to establish an ad hoc mesh network across the first and second implantable medical devices using ultrasound signals, wherein the first and second implantable medical devices are client implants, and wherein the host device is configured to actuate one or more of the client implants.

15. The system of claim 14, wherein the host device is configured to receive data from one or more of the client implants.

16. The system of claim 15, wherein the host device is an implant.

17. The system of claim 15, wherein the host device is an external device.

* * * * *